US008501179B2

(12) United States Patent
Numata et al.

(10) Patent No.: US 8,501,179 B2
(45) Date of Patent: Aug. 6, 2013

(54) ANTIBODY AGAINST PCRV

(75) Inventors: Yoshito Numata, Osaka (JP); Yoshinori Yamano, Osaka (JP); Takafumi Sato, Toyonaka (JP); Toshinaga Tsuji, Sapporo (JP)

(73) Assignee: Shionogi & Co., Ltd., Osaka (JP)

( * ) Notice: Subject to any disclaimer, the term of this patent is extended or adjusted under 35 U.S.C. 154(b) by 287 days.

(21) Appl. No.: 12/863,983

(22) PCT Filed: Jan. 8, 2009

(86) PCT No.: PCT/JP2009/050118
§ 371 (c)(1),
(2), (4) Date: Jul. 21, 2010

(87) PCT Pub. No.: WO2009/088032
PCT Pub. Date: Jul. 16, 2009

(65) Prior Publication Data
US 2011/0150896 A1 Jun. 23, 2011

(30) Foreign Application Priority Data
Jan. 10, 2008 (JP) .................................. 2008-003214

(51) Int. Cl.
*A61K 39/40* (2006.01)
(52) U.S. Cl.
USPC ....................................................... 424/141.1
(58) Field of Classification Search
None
See application file for complete search history.

(56) References Cited

U.S. PATENT DOCUMENTS

| 6,551,795 | B1 | 4/2003 | Rubenfield et al. |
| 2004/0208888 | A1 | 10/2004 | Frank et al. |
| 2005/0063985 | A1 | 3/2005 | Frank et al. |
| 2009/0117121 | A1 | 5/2009 | Tanaka et al. |
| 2011/0150896 | A1 | 6/2011 | Numata et al. |

FOREIGN PATENT DOCUMENTS

| EP | 2011867 A1 | 1/2009 |
| EP | 2175017 A1 | 4/2010 |
| WO | WO-02/064161 A2 | 8/2002 |
| WO | WO-2004/099250 A1 | 11/2004 |
| WO | WO 2005/069970 A2 | 8/2005 |
| WO | WO-2007/114340 A1 | 10/2007 |
| WO | WO-2009/073631 A2 | 6/2009 |
| WO | WO-2009/088032 A1 | 7/2009 |
| WO | WO-2010/104052 A1 | 9/2010 |

OTHER PUBLICATIONS

European Search Report issued Jan. 28, 2011 in corresponding Application No. EP09701235.5—PCT/JP2009050118.
Neely, A.N. et al., "Passive anti-PcrV treatment protects burned mice against *Pseudomonas aeruginosa* challenge", Burns, vol. 31, No. 2, pp. 153-158, 2005.—XP004729362.
Kipnis, E. et al., "Targeting mechanisms of *Pseudomonas aeruginosa* pathogenesis", Medecine et Maladies Infectieuses, vol. 36, No. 2, pp. 78-91, 2006.—XP025087331.
Spack, E.G. et al., "Humanized Anti-Perv Monoclonal Antibody IM166 Binds to the Type III Toxin Delivery System of *Pseudomonas aeruginosa* and Prevents Mortality in an Animal Model of *Pseudomonas*-Induced Pneumonia", FASEB Journal, vol. 16, No. 4, 2002.—XP008007107.
Moss, J. et al., "Sera from adult patients with cystic fibrosis contain antibodies to *Pseudomonas aeruginosa* type III apparatus", Infection and Immunity, vol. 69, No. 2, pp. 1185-1188, 2001.—XP002615882.
Baer, M. et al., "An engineered human antibody fab fragment specific for *Pseudomonas aeruginosa* PcrV antigen has potent antibacterial activity", Infection and Immunity, vol. 77, No. 3, pp. 1083-1090, 2009.—XP002581947.
European Search Report—EP09701235.5—PCT/JP2009050118.
Yahr, T. L., et al., "Identification of Type III Secreted Products of *Pseudomonas aeruginosa* Exoenzyme S Regulon," J. of Bacter., vol. 179, No. 22, pp. 7165-7168 (1997).
Sawa, T., et al., "Active and passive immunization with the *Pseudomonas V* antigen protects against type III intoxication and lung injury," Nat. Med., vol. 5, No. 4, pp. 392-398 (1999).
Shime, N., et al, "Therapeutic Administration of Anti-PcrV F(ab')$_2$ in Sepsis Associated with *Pseudomonas aeruginosa*," J. Immunol., vol. 167, pp. 5880-5886 (2001).
Imamura, Y., et al., "Effect of anti-PcrV antibody in a murine chronic airway *Pseudomonas aeruginosa* infection model," Eur. Respir. J., vol. 29, No. 5, pp. 965-968 (2007).
Faure, K., et al., "Effects of monoclonal anti-PcrV antibody on *Pseudomonas aeruginosa*-induced acute lung injury in a rat model," J. Immune Based Therapies & Vaccines, vol. 1, (2003).
Frank, D. W., et al., "Generation and Characterization of a Protective Monoclonal Antibody to *Pseudomonas aeruginosa* PcrV," J. Infect. Dis., vol. 186, pp. 64-73 (2002).
NCBI Sequence Revision History [online] AccessionAF010149.

*Primary Examiner* — Brian J Gangle
(74) *Attorney, Agent, or Firm* — Birch, Stewart, Kolasch & Birch, LLP.

(57) ABSTRACT

Provided is an effective means for therapy of infection, particularly infection with *Pseudomonas aeruginosa*. Provided are a monoclonal antibody against PcrV or a part thereof, and a pharmaceutical composition containing the same as an active ingredient. Concretely, monoclonal antibody of the present invention has excellent inhibiting activity on cytotoxicity with respect to a target cell of *Pseudomonas aeruginosa*. Also, the monoclonal antibody of the present invention has high affinity with PcrV.

13 Claims, 11 Drawing Sheets

Figure 2

| Clone | Kd (M) |
|-------|--------|
| m166 | $3.0 \times 10^{-9}$ |
| 1F3 | $3.7 \times 10^{-10}$ |
| 2A4 | $3.5 \times 10^{-10}$ |
| 6F5 | $1.1 \times 10^{-10}$ |

Figure 10

(SEQ ID NO: 11, 12)

Heavy Chain

QVQLQQPGAELVKPGASVKLSCKASGYSFTSYWMHWVKQRPGQGLEWIGEINPSNGRTNYN
EKFNTKATLTVDTSSSTAYMQLSSLTSEDSAVYYCVLYGNYVVYYTMDYWGQGTSVTVSS

Light Chain

QIVLTQSPTIMSASLGEEITLTCSASTSVSYMEWYQQKSGTSPKILIYTTSKLASGVPSRFSGSGSG
TFYSLTISSVEAEDAADYYCHQWRNYPFTFGSGTKLEIKRAD

Figure 11

(SEQ ID NO: 13, 14)

Heavy Chain

DVQLQESGPGLVKPSQSLSLTCTVTGYSITSDYAWNWIRQFPGNKLEWMGYITYNGDTSYNPS
LKSRISIARDTSKNQFFLQLNSVTTEDTATYSCAGSRNYYGAWFAYWGQGTLVTVSA

Light Chain

DIVMTQSHKFMSTSIGDRVSINYKASQYVGTTVAWYQQKSGHSPKLLIYRASTRHTGVPDRFT
GSGSGTDFTLNISNVQSEDLADYFCQQYCSSPLTFGAGTYLEVKRAD

ANTIBODY AGAINST PCRV

The present application is a National Stage filing of PCT International Application No. PCT/JP2009/050118 filed on Jan. 8, 2009 under 35 U.S.C. §371, which in turn claims priority under 35 USC §119 (a)-(d) of Japanese Application No. 2008-003214 filed on Jan. 10, 2008.

TECHNICAL FIELD

The present invention relates to a monoclonal antibody that recognizes PcrV, or a part thereof. More specifically, the present invention relates to an antibody having higher neutralizing activity (hereinafter, also referred to as cytotoxicity inhibiting activity) than conventional anti-PcrV antibodies, or a part thereof, and a pharmaceutical composition containing the same.

BACKGROUND ART

*Pseudomonas aeruginosa* is obligately aerobic gram negative *bacillus* being widely existing in the natural world. Although its pathogenicity is usually low, it is a pathogen that causes opportunistic infections often occurring in patients suffering from various pre-existing diseases such as cancer and diabetes, and in patients administered with pharmaceuticals having immune-inhibitory action, and may often cause pneumonia, urinary tract infection, sepsis and the like to lead to severe results. In clinical fields, *pseudomonas aeruginosa* infection is considered as one of the most difficult infections to be treated because not only *Pseudomonas aeruginosa* has inherently low sensitivity to existent antibiotics, but also has high tendency to easily acquire resistance to various antibiotics and to become difficult to cure. Thus for *Pseudomonas aeruginosa*, the measure of developing new antibiotics one after another is limited, and a therapeutic method that does not rely on antibiotics is strongly desired.

High cytotoxicity of *Pseudomonas aeruginosa* is exerted by injection of toxin into a eukaryotic cell via a type III exotoxin secretion system. PcrV is a protein of 294 residues (NCBI Accession No. AAC45935, SEQ NO: 1) constituting the type III exotoxin secretion system, and an operon sequence encoding the same is open to the public (Patent document 1, Non-patent document 1). Since control for PcrV can possibly lead a therapeutic means in *pseudomonas aeruginosa* infection (Non-patent document 2), polyclonal antibodies (Non-patent documents 3, 4) and monoclonal antibodies (Patent document 2, Non-patent documents 5, 6) against PcrV having neutralizing activity are reported. However, polyclonal antibodies are difficult to be humanized and to be used as pharmaceutical compositions because of difficulty in improvement of antigenicity. Also the monoclonal antibodies having reported heretofore have low neutralizing activity and fail to satisfy requirements in clinical fields.

Patent document 1: U.S. Pat. No. 6,551,795
Patent document 2: Japanese Translation of PCT publication No. 2005-500250
Non-patent document 1: Yahr, T. L. et al., J. Bacteriol., 1997, vol. 179, p. 7165
Non-patent document 2: T. Sawa et al., Nature Medicine, 1999, vol. 5, p. 392
Non-patent document 3: Shime N et al., J. Immunol. 2001, vol. 167, p. 5880
Non-patent document 4: Imamura Y et al., Eur. Respir. J., 2007, Vol. 29, p. 965
Non-patent document 5: Karine Faure et al., J. Immune. Based. Therapies and Vaccines, 2003, Vol. 1
Non-patent document 6: Dara W. Frank et al., J. Infect. Disease, 2002, Vol. 186, p. 64

DISCLOSURE OF THE INVENTION

Problem to be Solved by the Invention

It is an object of the present invention to provide a measure that is effective in therapy of infection, in particular, infection with *pseudomonas aeruginosa*.

Means for Solving the Problem

As a result of diligent efforts on preparation of monoclonal antibody against PcrV, the present inventors have succeeded in preparing a novel monoclonal antibody which is considered to have higher therapeutic effect on disease, compared to a conventionally known anti-PcrV monoclonal antibody, and have completed the present invention.

To be more specific, the present invention relates to:
(1) a monoclonal antibody against PcrV or a part thereof, having at least one feature selected from:
    (A) inhibiting 50% or more of cytotoxicity to leukocyte cell of *Pseudomonas aeruginosa* at a concentration of 1 nM to 200 nM in vitro;
    (B) inhibiting 50% or more of cytotoxicity to myeloma cell of *Pseudomonas aeruginosa* at a concentration of 1 nM to 50 nM in vitro; and
    (C) having a dissociation constant (Kd) with PcrV of $2 \times 10^{-9}$ (M) or less;
(2) a monoclonal antibody or a part thereof, having amino acid sequence where complementarity determining region (CDR) of monoclonal antibody produced by either of hybridoma deposited as an accession number of FERM BP-11085, hybridoma deposited as an accession number of FERM BP-11086, hybridoma deposited as an accession number of FERM P-21405, and hybridoma deposited as an accession number of FERM P-21406;
(3) a monoclonal antibody or a part thereof, produced by either of hybridoma deposited as an accession number of FERM BP-11085, hybridoma deposited as an accession number of FERM BP-11086, hybridoma deposited as an accession number of FERM P-21405, and hybridoma deposited as an accession number of FERM P-21406;
(4) a monoclonal antibody against PcrV or a part thereof, having its epitope at positions 136 to 233 of amino acid sequence of SEQ ID NO: 1;
(5) a monoclonal antibody against PcrV or a part thereof, having 1) in a complementarity determining region, a heavy chain variable region including the following amino acid sequence: SFTSYWMH (SEQ ID NO: 15) INPSNGRTNYNEKFNT (SEQ ID NO: 16) YGNYVVYYTMDY (SEQ ID NO: 17) and 2) in a complementarity determining region, a light chain variable region including the following amino acid sequence: SASTSVSYME (SEQ ID NO: 18) TTSKLAS (SEQ ID NO: 19) HQWRNYPFT (SEQ ID NO: 20);
(6) a monoclonal antibody against PcrV or a part thereof, having 1) in a complementarity determining region, a heavy chain variable region including the following amino acid sequence: SITSDYAWN (SEQ ID NO: 21) YITYNGDTSYNPSLKS (SEQ ID NO: 22) SRNYYGAWFAY (SEQ ID NO: 23) and 2) in a complementarity determining region, a light chain variable region including the following amino acid sequence: KASQYVGTTVA (SEQ ID NO: 24) RASTRHT (SEQ ID NO: 25) QQYCSSPLT (SEQ ID NO: 26);

(7) a monoclonal antibody against PcrV or a part thereof, having 1) a heavy chain variable region having amino acid sequence of SEQ ID NO: 11, and 2) a light chain variable region having amino acid sequence of SEQ ID NO: 12;

(8) a monoclonal antibody against PcrV or a part thereof, having 1) a heavy chain variable region having amino acid sequence of SEQ ID NO: 13, and 2) a light chain variable region having amino acid sequence of SEQ ID NO:14;

(9) a pharmaceutical composition comprising the antibody or a part thereof according to any one of (1) to (8), as an active ingredient; and

(10) a hybridoma producing the antibody or a part thereof according to any one of (1) to (8).

Effect of the Invention

A monoclonal antibody or a part thereof of the present invention is useful as a therapeutic agent of infection because of its very excellent neutralizing activity on PcrV.

BRIEF EXPLANATION OF DRAWINGS

FIG. 2 shows affinities of PcrV antibodies (1F3, 2A4, 6F5, 7A7 and Mab166) determined by surface plasmon resonance analysis.

FIG. 10 shows amino acid sequence of a variable region of 1F3 antibody. The underline indicates a CDR region.

FIG. 11 shows amino acid sequence of a variable region of 2A4 antibody. The underline indicates a CDR region.

BEST MODE FOR CARRYING OUT THE INVENTION

Figure 1:
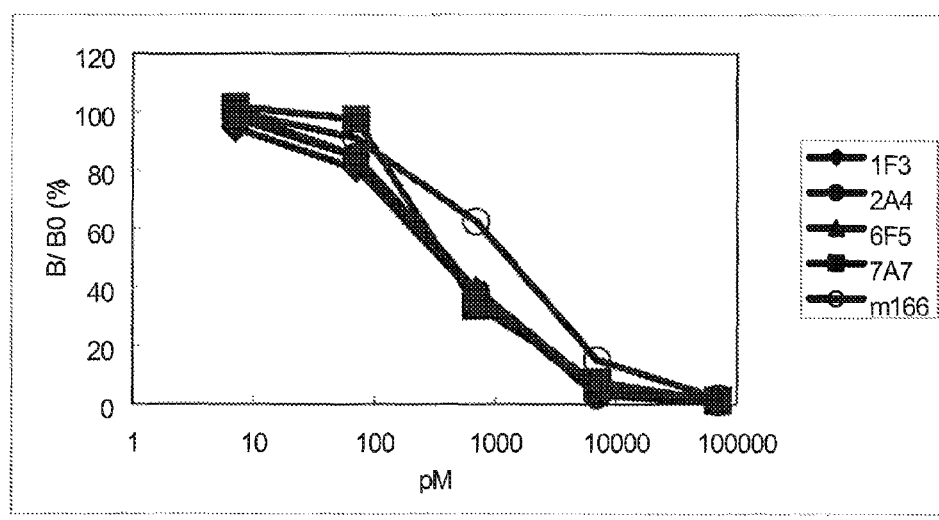
FIG. 1 shows curves in which biotin-labeled PcrV is substituted by non-labeled PcrV in PcrV antibodies (1F3, 2A4, 6F5, 7A7 and Mab166).

"Monoclonal antibody" which is an object of the present invention is a monoclonal antibody that specifically binds to the above-mentioned PcrV. More concretely, it is a monoclonal antibody against PcrV having at least one feature selected from (1) inhibiting 50% or more of cytotoxicity to leukocyte cell by *Pseudomonas aeruginosa* at a concentration of 1 nM to 200 nM in vitro; (2) inhibiting 50% or more cytotoxicity to myeloma cell by *Pseudomonas aeruginosa* at a concentration of 1 nM to 50 nM in vitro; and (3) having a dissociation constant (Kd) with PcrV of $2\times10^{-9}$ (M) or less.

One feature of the monoclonal antibody of the present invention is to have strong cytotoxicity inhibiting activity. For example, when leukocyte cell is used, the monoclonal antibody has such inhibiting (neutralizing) activity that inhibits 50% or more cytotoxicity of *Pseudomonas aeruginosa*, at a concentration range from 1 to 200 nM, preferably from 2 to 100 nM, and more preferably from 5 to 25 nM. When myeloma cell is used, the monoclonal antibody has such inhibiting (neutralizing) activity that inhibits 50% or more cytotoxicity of *Pseudomonas aeruginosa*, at a concentration range from 1 to 50 nM, preferably from 2 to 30 nM, and more preferably from 4 to 20 nM. These values largely exceed the numerical activities for Mb166 reported in Dara W. Frank et al. (J. Infect. Disease, 2002, Vol. 186, p. 64).

Another feature of the monoclonal antibody of the present invention is to have its epitope in a region from positions 136 to 233 in full-length amino acid sequence of PcrV (SEQ NO: 1). The present inventors have found that an antibody that recognizes this region has stronger activity (cytotoxicity inhibiting activity) than an antibody that recognizes other region.

Recognition epitope of monoclonal antibody may be identified in the following manner. First, a variety of partial structures of a molecule to be recognized by the monoclonal antibody are prepared. For preparation of partial structures, a method of preparing various partial peptides of the molecule with a known oligopeptide synthesis technique, a method of producing them in or out of host such as *E. coli* by incorporating into a suitable expression plasmid a DNA sequence encoding an objective partial peptide with a gene recombination technique, and the like are known, however, it is general to use combination of these methods for the aforementioned object. For example, after preparing a series of polypeptides shortened in an appropriate length from C terminal or N terminal of antigen protein by using a gene recombination technique well-known by a person skilled in the art, reactivity of monoclonal antibody with these polypeptides is examined and a recognition site is roughly determined.

Thereafter, a variety of oligopeptides of the corresponding part, mutants of the peptide, or the like are synthesized more finely by using an oligopeptide synthesis technique well-known by a skilled person in the art, and determination of epitope is made by examining bindability of a monoclonal antibody containing a prophylactic or therapeutic agent of the present invention as an active ingredient, with these peptides, or by examining competitive inhibiting activity of these peptides to binding between the monoclonal antibody and antigen. As a convenient method for obtaining a variety of oligopeptides, a commercially available kit (For example, SPOTs kit (available from Genosys Biotechnologies, Inc.), or a series of multipin/peptide synthesis kit with a multipin synthesis method (available from Chiron Corporation) may also be used.

Cytotoxicity inhibiting activity may be measured in the following manner. First, a monoclonal antibody for which cytotoxicity inhibiting activity is to be measured is diluted into appropriate concentrations in 2-fold dilution series.

Next, cells that are influenced by toxin of *Pseudomonas aeruginosa* or the like (hereinafter, referred to as target cells) are diluted, for example, by using a culture medium for cell culture, to achieve an appropriate number. Concretely, it is preferred to adjust into $3\times10^6$ to $5\times10^6$ cells/mL when myeloma cells are used, and to adjust to $1\times10^6$ to $3\times10^6$ cells/mL when leukocyte cells are used. Likewise, *Pseudomonas aeruginosa* cells are also adjusted to $1\times10^7$ to $5\times10^8$ cfu/mL using, for example, a culture medium. In the presence of the monoclonal antibody, *Pseudomonas aerugi-* nosa cells and target cells are cultured in the same test tube or well (for example, in vitro condition such as a well on a micro plate) in an appropriate culture condition. The culture condition at this time may be a commonly employed culture condition considered as being suited for growth of cells or bacteria. As for the culture time, optimum condition is appropriately changed depending on the kind of target cells, and for example, about 1 to 3 hour(s) for the case of using myeloma cells, and about 1 to 3 hour(s) for the case of using leukocyte cells are preferred. Taking a well not added with an antibody as a control group, a concentration at which 50% inhibition compared to the control group (effective concentration) is observed is calculated. As for decision of live and death of target cells, although various procedures have been established, for example, measurement of absorbance at an appropriate wavelength (for example, 400 to 500 nm) after addition of a coloring reagent is useful (See Nature Medicine 1999, vol.5, p. 392-395, for reference).

One feature of the monoclonal antibody of the present invention is to have high affinity with PcrV. Dissociation constant (Kd) which is used as an index of affinity with antibody of monoclonal antibody may be analyzed in various ways. For example, analysis can be readily conducted according to Scatchard method using an antigen labeled with various labeling agents, or a method using a commercially available measurement kit Biacore X (available from Amersham Pharmacia) or a similar kit according to the instruction manual and experimentation protocol attached to the kit. Dissociation constant (Kd value) determined using such a method is represented in a unit of M (mol). The smaller the dissociation constant of the tested monoclonal antibody, the stronger affinity the tested monoclonal antibody has. As to the monoclonal antibody of the present invention or a part thereof, dissociation constant (Kd) of PcrV is $2 \times 10^{-9}$(M) or less, preferably $1.5 \times 10^{-9}$(M) or less, and more preferably $1.2 \times 10^{-9}$(M) or less.

In the monoclonal antibody of the present invention, preferably, variable regions of heavy chain and light chain are derived from human, and may have a sequence of a modified body of SEQ ID NOs.11 to 14 (for example, unlimitedly including those having substitution, insertion, addition or deletion of one or several amino acid). Constant region domain preferably includes an appropriate human constant region domain (for example, those described in Kabat E. A. et al., US Department of Health and Human Services, Public Health Service, National Institute of Health). Through homology check by applying amino acid sequence of variable region to database of amino acid sequence of antibody prepared by Kabat et al. ("sequence of Proteins of Immunological Interest" US Dept. Health and Human Services, 1983), a CDR region will be found. As for the sequence of CDR region, a modified body with at least one addition, insertion, substitution or deletion may be embraced in the present invention as far as a bioactivity (for example, binding activity or neutralizing activity) requested in the present invention is maintained. Sequences having homology with each CDR region of 90 to 100% are recited. Preferably, sequences having homology of 95 to 100% are recited. More preferably, sequences having homology of 98 to 100% are recited.

Framework region may be related with any kind of framework region, and is preferably derived from human. Appropriate framework regions may be selected with reference to the document of Kabat E. A. et al. Preferable heavy chain framework is a human heavy chain framework, and for example, a framework of anti-PcrV antibody shown in FIG. 10 or FIG. 11. This may be determined from the sequence shown in FIG. 10 or FIG. 11 by referring to the above document. In a similar manner, an anti-PcrV light chain framework may be determined from the sequence shown in FIG. 10 or FIG. 11 by referring to the above document.

In the monoclonal antibody of the present invention, as a more preferred mode, included can be an antibody containing at least a) (i) an immunoglobulin heavy chain variable region ($V_H$) or a fragment thereof containing CDR1, CDR2 and CDR3 which are complementarity determining regions in its sequence wherein CDR1 has an amino acid sequence SFTSYWMH (SEQ ID NO: 15), CDR2 has an amino acid sequence INPSNGRTNYNEKFNT (SEQ ID NO: 16) and CDR3 has an amino acid sequence YGNYVVYYTMDY (SEQ ID NO: 17), and (ii) a constant part of human heavy chain or a fragment thereof.

Then, b) it is preferred to contain (i) an immunoglobulin light chain variable region ($V_L$) wherein CDR1 has an amino acid sequence SASTSVSYME (SEQ ID NO: 18), CDR2 has an amino acid sequence TTSKLAS (SEQ ID NO: 19) and CDR3 has an amino acid sequence HQWRNYPFT (SEQ ID NO: 20), and (ii) a constant part of human light chain or a fragment thereof.

Further, as a more preferred anti-PcrV antibody of the present invention, included can be an antibody containing at least a) (i) an immunoglobulin heavy chain variable region ($V_H$) or a fragment thereof containing CDR1, CDR2 and CDR3 which are complementarity determining regions in its sequence wherein CDR1 has an amino acid sequence SITSDYAWN (SEQ ID NO: 21), CDR2 has an amino acid sequence YITYNGDTSYNPSLKS (SEQ ID NO: 22) and CDR3 has an amino acid sequence SRNYYGAWFAY (SEQ ID NO: 23), and (ii) a constant part of human heavy chain or a fragment thereof.

Then, b) it is preferred to contain (i) an immunoglobulin light chain variable region ($V_L$) wherein CDR1 has an amino acid sequence KASQYVGTTVA (SEQ ID NO: 24), CDR2 has an amino acid sequence RASTRHT (SEQ ID NO: 25) and CDR3 has an amino acid sequence QQYCSSPLT (SEQ ID NO: 26), and (ii) a constant part of human light chain or a fragment thereof.

The monoclonal antibody of the present invention may be prepared by an existent commonly used production method using PcrV (natural body, recombinant body, synthetic body and so on) as an immunogen. Concretely, first, a mammal, preferably, mouse, rat, hamster, guinea pig, rabbit, cat, dog, pig, goat, sheep, donkey, horse or bovine (including transgenic animals created to produce antibody derived from other animal, like human antibody producing transgenic mouse), more preferably mouse, rat, hamster, guinea pig or rabbit is immunized with PcrV serving as an immunogen, together with Freund's adjuvant as necessary, by one or several times of subcutaneous, intramuscular, intravenous, intrafootpad or intraperitoneal injection. Usually, immunization is conducted once to four times every about 1 to 21 days after primary immunization, and antibody producing cells may be acquired from the immunized mammal after about 1 to 10 days from the final immunization. The number of times and time interval of immunization may be appropriately changed depending on the property of the immunogen being used.

Examples of PcrV used as an immunogen or a hapten are as follows.
(A) Cells expressing PcrV on cell surface, or cell strains artificially established to express PcrV on cell surface, or gene recombinant cells created by using a gene recombination technique to express PcrV on cell surface;
(B) Supernatant of culture obtained by culturing gene recombinant cells created by gene recombination technique to express PcrV or a part thereof as protein, or PcrV or a part thereof purified from the supernatant of culture; or (C) Chemically synthesized PcrV or a part thereof.

Hybridoma that secrets monoclonal antibody may be prepared according to the Kohler and Milstein's method (Nature, 1975, vol. 256, p. 495-497) and a corresponding method. That is, hybridoma may be prepared by cell fusion between an antibody producing cell contained in spleen, lymph node, bone marrow, tonsil or the like, preferably in spleen acquired from a mammal immunized as described above, and a myeloma cell lacking autoantibody producing ability derived, preferably from a mammal such as mouse, rat, guinea pig, hamster, rabbit or human, more preferably from mouse, rat or human.

As a myeloma cell used in cell fusion, generally, cell lines obtained from mouse, for example, 8-azaguanidine resistant mouse (derived from BALB/c) myeloma strain P3X63Ag8U.1 (P3-U1) [Yelton, D. E. et al., Current Topics in Microbiology and Immunology, 81, 1-7 (1978)], P3/NSI/1-Ag4-1(NS-1) [Kohler, G. et al. European J. Immunology, 6, 511-519 (1976)], SP2/O-Ag14 (SP-2) [Shulman, M. et al. Nature, 276, 269-270 (1978)], P3X63Ag8, 653(653) [Kearney, J. F. et al. J. Immunology, 123, 1548-1550 (1979)], P3X63Ag8(X63) [Horibata, K. and Harris, A. W. Nature, 256, 495-497 (1975)] and the like may be used.

Hybridoma that produces monoclonal antibody is screened by culturing a hybridoma, for example, in a microtiter plate, measuring reactivity to an immunogen used in mouse immunization as described above in culture supernatant in the well where proliferation is observed, by an immune measuring method such as RIA or ELISA, and selecting a clone that produces a monoclonal antibody exhibiting specific affinity with the immunogen or hapten. Then, usually used is a non-competitive ELISA wherein an immunogen is solid-phased, and an antibody in culture supernatant that binds to the solid-phased immunogen is detected by an anti-mouse secondary antibody labeled with enzyme.

Production of monoclonal antibody from hybridoma may be achieved by culturing hybridoma in vitro or in ascites of mouse, rat, guinea pig, hamster or rabbit, preferably of mouse or rat, or more preferably of mouse, followed by isolation from the obtained culture supernatant or ascites of mammal. In the case of in vitro culture, the hybridoma may be cultured in a known nutrient medium or in any nutrient cultures derived and prepared from a known base medium used for proliferating, maintaining and storing hybridoma and for producing monoclonal antibody in culture supernatant, depending on various conditions such as property of cultured cell species, object of the test research and culturing method.

As a base medium, for example, low-calcium media such as Ham'F12 medium, MCDB153 medium or low-calcium MEM culture, and high-calcium media such as MCDB104 medium, MEM medium, D-MEM medium, RPMI1640 medium, AF104 medium, or RD medium can be recited, and such a base medium may contain, for example, serum, hormone, cytokine and/or various inorganic or organic substances depending on the object. Isolation and purification of monoclonal antibody may be achieved by subjecting the culture supernatant or ascites as described above to saturated ammonium sulfate, ion exchange chromatography (e.g., DEAE or DE52), affinity column chromatography such as anti-immunoglobulin column or protein A column or the like.

As a monoclonal antibody of the present invention, a recombinant antibody that is produced using gene recombination technique in such a manner that an antibody gene is cloned from antibody producing cell, for example, hybridoma, and incorporated into an appropriate vector, and the vector is introduced into a host may be used (for example, Carl et al., THERAPEUTIC MONOCLONAL ANTIBODIES, published in 1990).

Concretely, from a hybridoma that produces an objective antibody, or from an immune cell that produces an antibody, for example, from a cell obtained by immortalizing sensitized lymphocyte or the like by cancer gene or the like, mRNA encoding a variable region (V region) of antibody is isolated. In isolation of mRNA, whole RNA is prepared by a known method, for example, by guanidine ultracentrifugation (Chirgwin, J. M. et al., Biochemistry (1979) 18, 5294-5299) or the like, and mRNA is prepared by using mRNA Purification Kit (available from Pharmacia) or the like.

From the obtained mRNA, cDNA of antibody V region is synthesized using a reverse transcriptase. Synthesis of cDNA may be conducted using AMV Reverse Transcriptase First-strand cDNA Synthesis Kit or the like. Further, for synthesis and amplification of cDNA, 5'-Ampli FINDER RACEKit (available from Clonetech) and 5'-RACE method using PCR (Frohman, M. A. et al, Proc. Natl. Acad. Sci. USA 1988, vol. 85, p. 8998) may be used. An objective DNA fragment is purified from the obtained PCR product, and connected with vector DNA. A recombinant vector is thus created and introduced into E. coli or the like, and a colony is selected and a desired recombinant vector is prepared. DNA base sequence of objective DNA is verified by a known method, for example, by deoxy method.

If DNA encoding V region of objective antibody is obtained, the DNA is connected with DNA encoding a desired antibody constant region (C region), and incorporated into an expression vector. Alternatively, DNA encoding V region of antibody may be incorporated into an expression vector containing DNA of antibody C region. For production of antibody used in the present invention, antibody gene is incorporated into an expression vector in such a manner that it is expressed under control of an expression control region, for example, enhancer/promoter. Next, a host cell can be transformed with this expression vector to cause expression of antibody.

For expression of antibody gene, heavy chain (H chain) or light chain (L chain) of antibody may be separately incorporated into expression vectors, or a host may be co-transformed with these expression vectors, or DNA encoding H chain and L chain may be incorporated into a single expression vector to transform a host with the resultant expression vector (see WO94/11523).

Monoclonal antibody of the present invention includes gene recombinant-type monoclonal antibodies that are artificially modified for the purpose of lowering heterologous antigenicity against human, for example, chimera monoclonal antibody, humanized monoclonal antibody and human monoclonal antibody.

Chimera monoclonal antibody is composed of V region derived from antibody of a mammal other than human and C region derived from human antibody, and humanized monoclonal antibody is composed of CDR derived from antibody of a mammal other than human and FR and C regions derived from human antibody, and these monoclonal antibodies are useful as an antibody used in the present invention since antigenicity in human body is reduced. These modified monoclonal antibodies may be produced using known method.

chimera monoclonal antibody is obtained by connecting DNA encoding antibody V region obtained as described above with DNA encoding human antibody C region, incorporating the resultant DNA into an expression vector, and introducing the expression vector into a host to cause production (for example, WO95/14041). Using this known method, chimera monoclonal antibody useful in the present invention may be obtained.

Humanized monoclonal antibody is obtained by transplanting a complementarity determining region (CDR) of antibody of a mammal other than human, for example, of a mouse, into CDR of human antibody, and a general gene recombinant technique for this is also known (for example, WO95/14041).

Concretely, a DNA sequence designed so that CDR of mouse antibody and framework region (FR) of human antibody are connected is synthesized by PCR method from several oligonucleotides prepared to have overlapping parts in their terminals. The obtained DNA is connected with DNA encoding human antibody C region and incorporated into an expression vector, and the resultant expression vector is introduced into a host to cause production (for example, WO95/14041).

As FR of human antibody connected via CDR, the one in which CDR forms a good antigen binding site is selected. As necessary, amino acid of FR in V region of antibody may be substituted so that the reconstructed CDR of human antibody forms an appropriate antigen binding site (Sato, K. et al., Cancer Res. 1993, vol. 53, p. 851). In a chimera monoclonal antibody and a humanized monoclonal antibody, human antibody C region is used. As a preferred human antibody C region, C$\gamma$ can be recited, and for example, C$\gamma$1, C$\gamma$2, C$\gamma$3 and C$\gamma$4 may be used. Further, for improving stability of antibody or its production, human antibody C region may be modified.

Human monoclonal antibody is composed of V region and C region derived from human antibody, and may be produced by immunizing a human antibody producing transgenic non-human mammal such as human antibody producing transgenic mouse (for example, WO94/25585) with an immunogen, according to an existent general production method of monoclonal antibody.

In the present invention, the phrase "part of monoclonal antibody" means a region that is a part of the aforementioned monoclonal antibody of the present invention and has specific bindability to PcrV likewise the monoclonal antibody (hereinafter, also referred to as simply "antibody fragment").

Concretely, Fab (fragment of antigen binding), F(ab')$_2$, Fab', single chain antibody (single chain Fv; hereinafter denoted by scFv), disulfide stabilized antibody (disulfide stabilized Fv; hereinafter denoted by dsFv), dimerized V region fragment (hereinafter, denoted by Diabody), peptide containing CDR, having specific bindability to the PcrV, can be recited (Expert opinion on therapeutic patents, vol. 6, No. 5, p. 441-456, 1996).

Fab is an antibody fragment having a molecular weight of about 50,000 with antigen binding activity, made up of about a half of N-terminal side of H chain and whole L chain, obtained by degrading with an enzyme papain a peptide part above two disulfide bonds (S—S bond) cross-linking two H chains in hinge region of IgG. Fab used in the present invention may be obtained by treating the monoclonal antibody of the present invention with papain. Alternatively, Fab may be produced by inserting DNA encoding Fab of monoclonal antibody of the present invention into an expression vector for cell and by introducing the vector into a cell to cause expression.

F(ab')$_2$ is an antibody fragment having a molecular weight of about 100,000 with antigen binding activity, formed by binding two Fab' regions in a hinge part. These Fab' regions are obtained by pepsin degradation below two S—S bonds of hinge region of IgG. The F(ab')$_2$ used in the present invention may be obtained by treating the monoclonal antibody of the present invention with pepsin. Alternatively, F(ab')$_2$ may be produced by inserting DNA encoding F(ab')$_2$ of the monoclonal antibody into an expression vector for cell and by introducing the vector into E. coli, yeast or animal cell to cause expression.

Fab' is an antibody fragment having a molecular weight of about 50,000 with antigen binding activity, obtained by cutting S—S bond between hinges of the aforementioned F(ab')$_2$. Fab' used in the present invention may be obtained by treating F(ab')$_2$ of monoclonal antibody of the present invention with a reducing agent, dithiothreitol. Alternatively, Fab' may be produced by inserting DNA encoding Fab' of the monoclonal antibody into an expression vector for cell and by introducing the vector into E. coli, yeast or animal cell to cause expression.

scFv is VH-P-VL or VL-P-VH peptide in which one VH chain and one VL chain are connected using an appropriate peptide linker (hereinafter, denoted by P), and is an antibody fragment having antigen activity. VH and VL contained in scFv used in the present invention may be derived from the monoclonal antibody of the present invention. scFv used in the present invention may be produced by acquiring cDNA encoding VH and VL from hybridoma producing a monoclonal antibody of the present invention, constructing a scFv expression vector, and causing expression by introducing the expression vector into E. coli, yeast or animal cell.

dsFv refers to one obtained by binding polypeptides, in which each one amino acid residue is substituted with a cysteine residue in VH and VL, via S—S bond. The amino acid to be substituted with cysteine residue may be selected based on tertiary structure prediction of antibody according to the method indicated by Reiter et al. (Protein Engineering, 7, 697 (1994)). VH or VL contained in dsFv used in the present invention may be derived from the monoclonal antibody of the present invention. dsFv used in the present invention may be produced by acquiring cDNA encoding VH and VL from hybridoma producing a monoclonal antibody of the present invention, constructing a dsFv expression vector by inserting it into an appropriate expression vector, and causing expression by introducing the expression vector into E. coli, yeast or animal cell.

Diabody is an antibody fragment where a dimer of scFvs having the same or different antigen binding specificity is formed, and is an antibody fragment having bivalent antigen binding activity for the same antigen or two antigen binding activities specific for different antigens. For example, bivalent Diabody that specifically reacts with the monoclonal antibody of the present invention may be produced by acquiring cDNA encoding VH and VL of a monoclonal antibody of the present invention, constructing DNA encoding scFv having a peptide linker of 3 to 10 residues, inserting the DNA into an expression vector for cell, and causing expression of Diabody by introducing the resultant expression vector into E. coli, yeast or animal cell.

Peptide containing CDR includes at least one region of CDR of VH or VL. Plural CDRs may be combined directly or via an appropriate peptide linker. Peptide containing CDR used in the present invention may be produced by acquiring cDNA encoding VH and VL of a monoclonal antibody of the present invention, constructing DNA encoding CDR, inserting the DNA into an expression vector for animal cell, and causing expression by introducing the resultant expression vector into E. coli, yeast or animal cell. Peptide containing CDR may also be produced by chemical synthesis method such as Fmoc method (fluorenyl methyloxycarbonyl method) or tBoc method (t-butyloxycarbonyl method).

A monoclonal antibody of the present invention or a part thereof may be modified insofar as it is suitably used in the present invention. As a modified substance, antibodies bound to various molecules including polyethylene glycol (PEG) and the like may be used. Modification made on antibody may be modification by introduction of chemical bond, or may be modification made on amino acid sequence of the antibody. A monoclonal antibody of the present invention or a part thereof also embraces these antibody modified substances. For obtaining such antibody modified substances, the obtained antibody may be modified. These techniques have been already established in the art.

A monoclonal antibody of the present invention and a part thereof is useful as a pharmaceutical composition. Therefore, a pharmaceutical composition containing a monoclonal antibody of the present invention and a part thereof may be administered systemically or topically by in an oral or parenteral route. For parenteral administration, for example, intravenous injection such as drip infusion, intramuscular injection, intraperitoneal injection, subcutaneous injection, intranasal administration, inhalation and the like can be selected. However, since it is known that *Pseudomonas aeruginosa* will inflict damage particularly on lung epithelial cell and macrophage of pulmonary alveolus by respiratory tract infection (T. Sawa et al., Nature Medicine, 1999, vol. 5, p. 392), intranasal administration and inhalation are desired.

A pharmaceutical composition of the present invention is administered for therapy of a patient suffering from cystic fibrosis or infection by *Pseudomonas aeruginosa*. For example, effective dose is selected in the range of 0.01 mg to 100 mg per 1 kg of body weight per one time. Alternatively, a dose of 1 to 1000 mg, preferably a dose of 5 to 50 mg per a patient may be selected. However, a dose of the pharmaceutical composition containing the monoclonal antibody of the present invention or a part thereof is not limited to these doses. Administering duration may be appropriately selected depending on the age, symptom and the like of the patient. The pharmaceutical composition of the present invention may also include a pharmaceutically acceptable carrier or additive as well depending on the route of administration.

Examples of such carrier and additive include water, pharmaceutically acceptable organic solvent, collagen, polyvinyl alcohol, polyvinylpyrrolidone, sodium alginate, water-soluble dextran, pectin, methyl cellulose, ethyl cellulose, casein, diglycerin, propylene glycol, polyethylene glycol, Vaseline, human serum albumin (HSA), mannitol, sorbitol, lactose, and surfactants permitted as a pharmaceutical additive. An additive for use is appropriately selected or combined from the above depending on the dose form, but, it is not limited thereto.

REFERENCE EXAMPLE

Preparation of recombinant Mab166

For executing a comparative experiment, Mab166 (Japanese patent Application No. 2005-500250 or the like) was prepared as a recombinant antibody.

First, mRNA is extracted from hybridoma that produces an antibody classified into a subclass IgG2a, and constant regions of H chain and L chain were cloned by RT-PCR method. Each fragment amplified by PCR was inserted into NheI-NotI site of pcDNA3.1 (+) vector (available from Invitrogen Corporation), and a multi-cloning site was further incorporated for allowing a DNA fragment of variable region part to be inserted.

Next, after splitting gene sequence of H chain and L chain of Mab166 variable region part into four, sense DNA and antis-sense DNA of these were synthesized, and annealed. Fragments after annealing were caused to bind by DNA ligase, and cloning was made at MfeI-BlpI region for H chain, and at EcoRV-BsiWI region for L chain.

Vectors of H chain and L chain having identified base sequences were introduced into HEK 239T cell by using Lipofectamine 2000 (available from Invitrogen Corporation), and after 48 hours, a cell culture supernatant was collected. From the collected cell supernatant, recombinant Mab166 was purified through Protein-G (available from PIERCE) column.

The present invention will be concretely explained by way of the following non-limitative Examples. As a preparation technique of antibody, methods described in Immunochemistry in Practice (Blackwell Scientific Publications) were used unless otherwise specified. As a gene engineering technique, methods described in Molecular Cloning: A Laboratory Manual, 2nd Edition (Cold Spring Harbor Laboratory) were used unless otherwise specified.

Example 1

Preparation of Antigen

Chromosome DNA of *Pseudomonas aeruginosa* standard strain PAO1 provided from Tokai University, Japan, was extracted, and gene encoding PcrV protein (SEQ ID NO: 2) was amplified by PCR using the DNA as a template. A recognition site of restriction enzyme SphI was provided in 5'-side primer and a recognition site of restriction enzyme HindIII was provided in 3'-side primer, (SEQ ID NOs: 3, 4), and in insertion into an expression vector a design was made so that cysteine is inserted between histidine tag and start codon for biotin labeling. The amplified PCR fragment was cloned into pWE30 vector (available from GE healthcare) at SphI and HindIII sites. After sequencing, the vector was introduced into *E. coli* JM109 to obtain recombinant *E. coli* (PcrV-JM109). PcrV-JM109 was cultured in 500 mL of LB/Ampicillin liquid culture medium at 37° C., and when OD600 reached 0.5, IPTG was added to a final 0.75 mM. After culturing at 37° C. for additional 1.5 hours, bacterial cells were centrifuged, and added with 15 mL of buffer A (25 mM Tris-HCl (pH 8.0), 0.5 M NaCl, 2 mM $MgCl_2$) containing 0.5% lysozyme (available from Sigma). After the incubation at 0° C. for 30 minutes, cells were sonicated. Following centrifugation, a soluble fraction was obtained, subjected to His-Bind Columns (available from Novagen), and then eluted with buffer B (20 mM phosphate buffer (pH 7.4), 500 mM NaCl) containing 200 mM imidazole. The final elution fraction was dialyzed against 10 mM phosphate buffer (pH 7.4) to replace the buffer.

Biotin Labeling of Antigen

PcrV protein expressed and purified as described above was allowed to react in a mercapto ethylamine solution of a final concentration of 10 mM at 37° C. for 150 minutes to reduce cysteine residue. PEO-maleimide activated biotin (available from PIERCE) was added in an amount of 20-fold by molar ratio with respect to reduced SH groups, and allowed to react overnight at 4° C., and then dialysis was conducted to remove unreacted biotin.

Immunization with Antigen

Each 20 μg of purified PcrV antigen was intraperitoneally immunized with complete Freund's adjuvant to seven Balb/c female mice aged at 4 weeks. Booster immunization was performed by administering 20 μg of PcrV with incomplete Freund's adjuvant after 14 days and 35 days. Further, final immunization was conducted after 77 days by intraperitoneal administration of 20 μg of PcrV and tail vein administration of 10 μg of PcrV.

Preparation of Hybridoma

Spleen was extirpated after 3 days from the final immunization, and spleen cells were collected. A spleen cell and a mouse myeloma cell (p3×63-Ag8.U1, Tokyo mass research laboratory) were fused by using 50% polyethylene glycol 4000, and selected in a culture medium containing hypoxanthine, aminopterin and thymidine.

Selection of PcrV Antibody

After 8 days from cell fusion, specific antibody producing cells were screened. Immunoassay used in screening was as follows. Each well of a 96-well microtiter plate (available from Nunc) was added with 200 μL of tris buffer (50 mM Tris-HCl, pH7.5) containing 2 μg of anti-mouse IgG antibody (available from Shibayagi) and immobilized for 16 hours at 4° C. These wells were washed twice with 300 μL of washing solution (saline containing 0.1% Tween 20), then added with 300 μL of blocking solution (50 mM Tris-HCl pH7.5, 2% BlockAce (available from Dainippon Sumitomo Pharma Co., Ltd.), 10% Sucrose) and left for two hours at room temperature. After washing each well twice with 300 μL of washing solution, 50 μL of hybridoma culture supernatant was diluted with 150 μL of buffer C (50 mM tris buffer, pH 7.6 containing 0.9% sodium chloride, 0.05% sodium azide, 0.5% bovine serum albumin, 0.01% Tween80, and 25 μM Diethylenetriamine-N,N,N',N'',N''-pentaacetic acid) and added to each well, and allowed to react overnight at 4° C. After washing three times with 300 μL of washing solution, 200 μL of buffer C containing 10 ng of Eu-Labeled Streptavidin (available from PERKIN ELMER) and 25 ng of biotin-labeled PcrV was added, and allowed to react for 1 hour at room temperature. After the reaction, washing three times with 300 μL of washing solution, and 200 μL of enhancement reagent (1.39 g/L potassium phthalate, 19.3 mg/L of Tri-n-octylphosphine oxide, 4.59 mg/L of 2-naphthoyltrifluoroacetone, 1.0 g/L of Triton-X100, 6.0 g/L of acetic acid) was added, and time-resolved fluorescence was measured.

From the result of screening, 20 clones of hybridoma which exhibited strong affinity with recombinant PcrV were selected, and cytotoxicity inhibition activity by *Pseudomonas aeruginosa* was examined according to Example 4. As a result, cytotoxicity inhibiting activity was observed in 10 clones, and these clones were then cloned twice by limiting dilution method, and thus hybridoma cells were selected. From the obtained 10 clones, 4 clones exhibited high cytotoxicity inhibition activity were selected, and named 1F3, 2A4, 6F5, and 7A7, respectively. For these antibodies, subclass of antibody was determined using mouse monoclonal antibody isotyping ELISA kit (available from BD Biosciences), and it was found that 1F3 was IgG2a, 2A4 was IgG2b, 6F5 was IgG2a, 7A7 was IgG2a.

Hybridomas cells that produce monoclonal antibodies 1F3, 2A4, 6F5 and 7A7 were deposited with National Institute of Advanced Industrial Science and Technology, International Patent Organism Depositary (Center No. 6, 1-1-1, Higashi, Tsukuba-shi, IBARAGI, JAPAN) on Oct. 18, 2007, under the accession numbers of FERM BP-11085, FERM BP-11086, FERM P-21405, and PERM P-21406, respectively.

Example 2

Binding Activity of Antibody

For measuring binding activity of antibodies (1F3, 2A4, 6F5, 7A7), competitive immunoassay was performed. Each well of a 96-well microtiter plate (available from Nunc) was added with 100 μL of tris buffer (50 mM Tris-HCl, pH7.5) containing 1.5 μg of anti-mouse Fc antibody (available from Jackson ImmunoResearch) and immobilized for 16 hours at 4° C. These wells were washed twice with 300 μL of washing solution, then added with 300 μL of blocking solution and left for two hours at room temperature to achieve blocking (anti-mouse IgG antibody solid-phased plate). After washing twice with 300 μL of washing solution, 2 ng/well of each antibody and non-labeled PcrV at five concentrations in 10-fold dilution series from 500 ng/well were added. Then, 5 ng/well of biotinylated PcrV was added and allowed to react overnight. After washing four times with 300 μL of washing liquid and adding with 100 μL/wel of Enhancement Reagent (available from PerkinElmer), time-resolved fluorescence was measured after stirring for 1 minute. As a result, 1F3, 2A4, 6F5 and 7A7 showed stronger binding activity against PcrV than Mab166 (FIG. 1).

Next, affinity of 1F3, 2A4, 6F5, 7A7 and Mab166 with PcrV was determined by surface plasmon resonance analysis. Anti-mouse IgG Fc antibody was immobilized on a CM5 sensor chip by using Mouse Antibody Capture Kit (available from BIACORE) in BIAcore T100 instrument. Sequentially, each PcrV antibody was captured, and recombinant PcrV was loaded to determine KD value.

As a result, every clone showed higher affinity than Mab166 as evidenced from the affinity of $3.7 \times 10^{-10}$ (M)for 1F3, the affinity of $3.5 \times 10^{-10}$ (M) for 2A4, the affinity of $1.1 \times 10^{-10}$ (M) for 6F5, and the affinity of $1.1 \times 10^{-9}$ (M) for 7A7, in contrast to the affinity of $3.0 \times 10^{-9}$ (M) for Mab166 (FIG. 2).

Example 3

Sandwich Immunoassay with Mab166

In order to prove that 1F3, 2A4, 6F5 and 7A7 have a different epitope from that of Mab166, sandwich immunoassay between each antibody and Mab166 was examined.

First, Mab166 was labeled with biotin. One hundred μg of Mab166 and 7.853 μg of NHS-PEO$_4$ Biotin (available from PIERCE) were mixed in 0.1M PBS (pH 7.4), and allowed to react for 2 hours on ice. Thereafter, biotinylated mAb was purified by size exclusion chromatography (G2000SW column (available from TOSOH)) to remove unreacted biotin from the reaction solution.

Sandwich immunoassay was performed as follows. Each well of a 96-well microtiter plate (available from Nunc) was added with 100 μL of PBS (−) solution each containing 500 ng of PcrV antibody (1F3, 2A4, 6F5, 7A7) and immobilized for 16 hours at 4° C. These wells were washed once with 300 μL of a washing solution, then added with 300 μL of blocking solution and left for two hours at room temperature to achieve blocking. After washing each well twice with 300 μL of washing solution, 100 μL of Assay Buffer (available from Wallac) containing 50 ng of PcrV and 50 ng of biotin-labeled Mab166 was added and allowed to react overnight at 4° C. After washing three times with washing solution, 100 μL of Assay Buffer containing 50 ng of Eu-Labeled Streptavidin (available from Wallac) was added, and allowed to react for 1 hour at room temperature. After washing three times with washing solution and adding 100 μL of Enhancement Reagent, stiffing for 1 minute, and then time-resolved fluorescence was measured.

Figure 3:
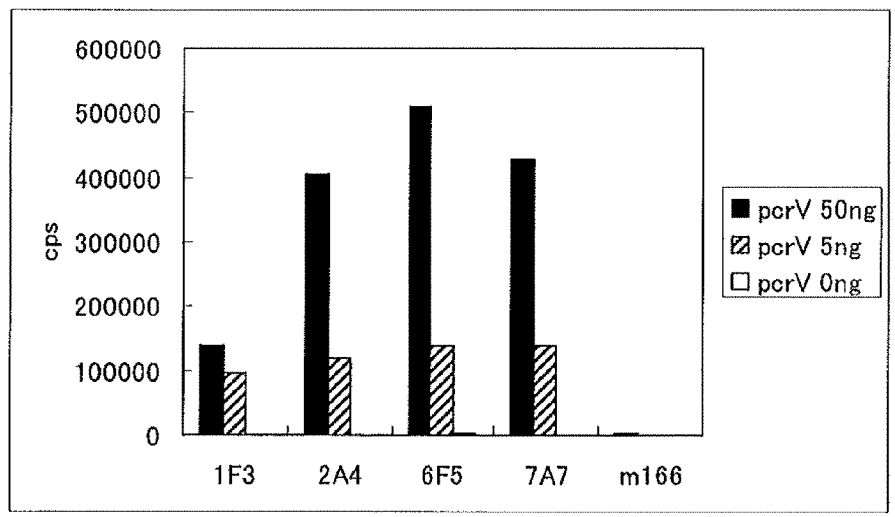
FIG. 3 shows results of sandwich assays between PcrV antibodies (1F3, 2A4, 6F5, 7A7 and Mab166) and Mab166.

As a result, sandwich immunoassay was possible between any of 1F3, 2A4, 6F5 and 7A7 and Mab166, so that it was revealed that the present antibodies had a different epitopes from that of Mab166 (FIG. 3).

Example 4

Measuring the Cytotoxicity Inhibition Activity of PcrV Antibodies

For 1F3, 2A4, 6F5 and 7A7, cytotoxicity inhibiting activity was measured. The method is as follows.

First, 1F3, 2A4, 6F5, 7A7 was diluted in 2-fold dilution series from 32 µg/mL, and 10 µL was dispensed into each well of 96-well microplate. Next, mouse myeloma cell P3U1 (from ATCC) was adjusted to 5×10$^6$ cells/mL or human leukocyte cell-line U937 (from ATCC) cell was adjusted to 1×10$^6$ cells/mL in a cell culture medium (RPMI1640 containing sodium hydrogen carbonate, and not containing L-glutamine and phenol red (available from Sigma)), and each 100 µL of cell suspension was added to the 96-well microplate. Further, *Pseudomonas aeruginosa* strain SR24 cultured overnight in Cation-adjusted Mueller Hinton Broth (Difco) was adjusted to 1×10$^8$ cfu/mL in a cell culture medium, and added in an amount of 10 µL/well, and cultured for 3 hours at 37° C. in the presence of 5% $CO_2$. After stiffing for 3 hours, each 10 µL of WST-8 (available from Kishida Chemical Co., Ltd.) was added, and cultured at 37° C. in the presence of 5% $CO_2$ for 3 hours for the case of myeloma cell P3U1, or for 1 hour for the case of U937 cell. After completion of culture, absorbance 450 nm was measured.

Figure 4:
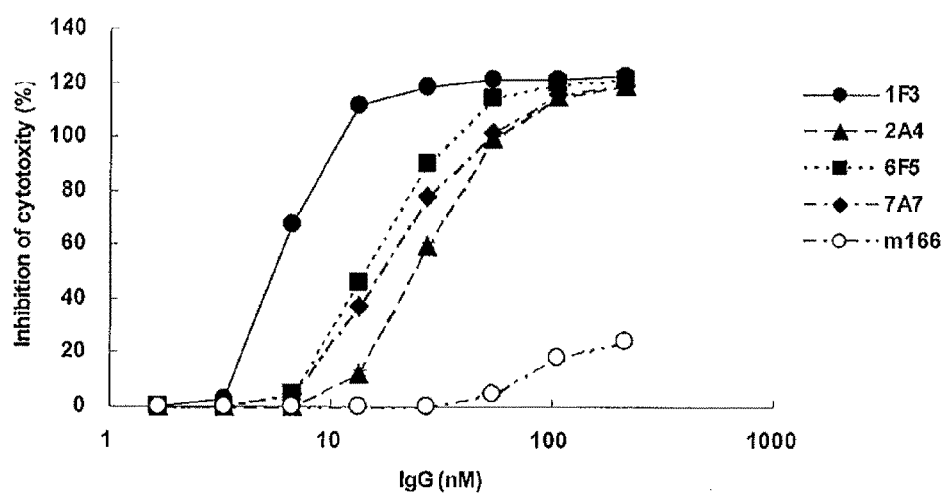
FIG. 4 shows inhibiting effects of PcrV antibodies (1F3, 2A4, 6F5, 7A7 and Mab166) on cytotoxicity to U937 cells of *Pseudomonas aeruginosa* strain SR24.
Figure 5:
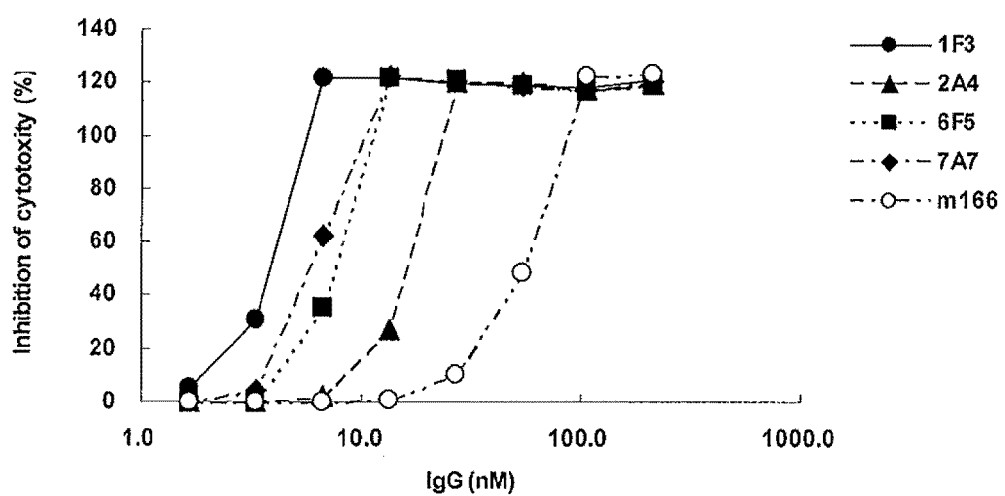
FIG. 5 shows inhibiting effects of PcrV antibodies (1F3, 2A4, 6F5, 7A7 and Mab166) on cytotoxicity to myeloma cells P3U1 of *Pseudomonas aeruginosa* strain SR24.

As a result, when leukocyte U937 cell was used, cytotoxicity inhibiting activity (IC50) was 5.3 nM for 1F3, 20.7 nM for 2A4, 12.7 nM for 6F5, and 14.7 nM for 7A7 in contrast to higher than 213 nM for Mab166, and when myeloma cell U3P1 was used, cytotoxicity inhibiting activity (IC50) was 4.0 nM for 1F3, 16 nM for 2A4, 7.3 nM for 6F5, and 6.0 nM for 7A7 in contrast to 54 nM for Mab166. That is, 1F3, 2A4, 6F5 and 7A7 had higher cytotoxicity inhibition activity for both cells than Mab166 which has been previously described (Frank et al., The Journal of Infectious Diseases, 2002, vol. 186, p. 66) (FIG. 4 and FIG. 5).

Example 5

Preparation of Truncated PcrV

Truncated PcrV (136-233) was prepared in the following manner.

A fragment amplified by PCR with 5'-side primer GCTCGAGGATCCCAAGGCGCTGACCGC (SEQ ID NO: 5) and 3'-side primer GTTAAGCTTCTCGAAGGGGTACTC (SEQ ID NO: 6) by using pQE30-PcrV being a PcrV antigen protein expression plasmid as a template was treated with restriction enzymes BamHI and HindIII, and inserted into pET32b (available from Novagen). After sequencing, the vector was introduced into *E. coli* strain BL21-DE3 to obtain recombinant *E. coli* (truncated PcrV-BL21). This expression strain was pre-cultured for a whole day and night at 37° C. in 2 mL of LB/Ampicillin liquid culture medium. Two mL of pre-culture liquid was added into 500 mL of LB/Ampicillin liquid culture medium and cultured at 37° C., and when OD600 reached 0.5, the culture liquid was kept still for 30 minutes on ice. IPTG was added to final concentration 0.75 mM, and cultured at 15° C. overnight. Bacterial cells were collected by centrifuging at 4° C., ×5000 g for 30 minutes. The supernatant was removed to other tube, and 10 mL of Buffer X (25 mM Tris-HCl (pH7.5), 150 mM NaCl, 2 mM $MgCl_2$) containing 0.1% lysozyme (available from Sigma) was added to the pellet and suspended, left still on ice for 1 hour, and then sonicated under cooling on ice. Then a soluble fraction was applied to a Ni-NTA column (Quiagen), and eluted with Buffer Y (25 mM Tris-HCl (pH 7.5), 150 mM NaCl, 200 mM Imidazole). The eluted fraction was dialyzed with 10 mM phosphate buffer (pH 7.4).

Determination of Epitope Region

Figure 6:
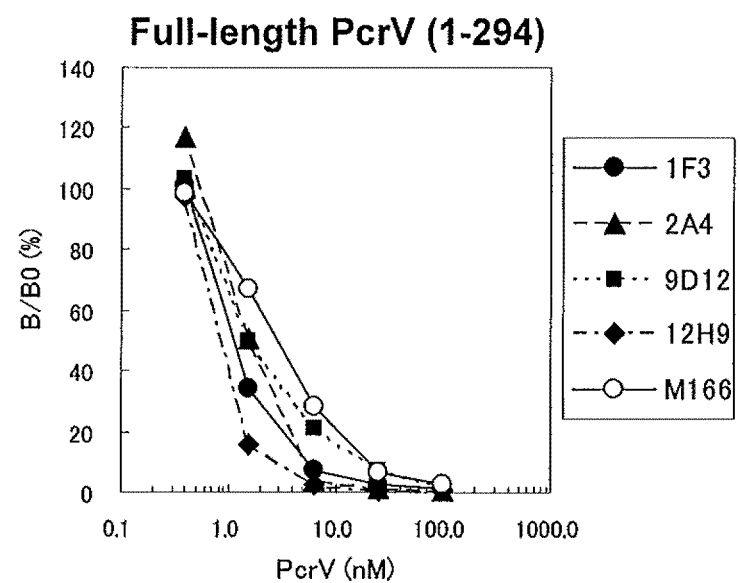
FIG. 6 shows curves in which biotin-labeled PcrV is substituted by non-labeled full-length PcrV and truncated PcrV in PcrV antibodies (1F3, 2A4, 9D12, 12H9 and Mab166).
Figure 6:
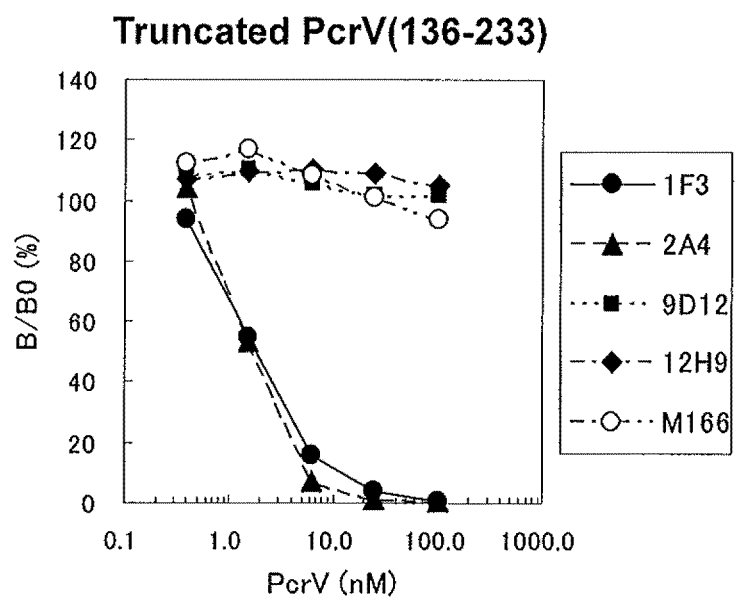

Each well of a 96-well microtiter plate (available from Nunc) was added with 150 µL of tris buffer (50 mM Tris-HCl, pH 7.5) containing 1.5 µg of anti-mouse IgG Fc antibody (available from Jackson ImmunoResearch) and immobilized for 16 hours at 4° C. These wells were washed twice with 300 µL of a washing solution, then added with 300 µL of blocking solution and left for two hours at room temperature to block each well. After washing each well once with 300 µL of washing liquid, each well was added with 50 µL of PcrV antibody solution diluted into a concentration of 80 ng/mL with Buffer C (50 mM tris buffer containing 0.9% sodium chloride, 0.05% sodium azide, 0.5% bovine serum albumin, 0.01% Tween 80, and 25 µM Diethylenetriamine-N,N,N',N", N"-pentaacetic acid, pH 7.6), followed by 50 µL of Eu-Labeled Streptavidin (available from PERKIN ELMER) solution diluted into a concentration of 200 ng/mL with Buffer C, 50 µL of truncated PcrV protein diluted in a given concentration with DELFIA Assay Buffer, and 50 µL of biotinylated PcrV solution diluted into a concentration of 1.0 µg/mL with Buffer C and allowed to react at 4° C. overnight. After washing three times with 300 µL of washing solution, 200 µL of an enhancement reagent (available from PERKIN ELMER) was added, and time-resolved fluorescence was measured (FIG. 6).

As a result, PcrV antibodies 1F3, 2A4, 9D12, 12H9, and recombinant Mab166, which is a model example of PcrV neutralizing antibody as previously described, exhibited reactivity with full-length PcrV (1-294). On the other hand, while 1F3 and 2A4 showed reactivity with PcrV (136-233), Mab166, as well as 9D12 and 12H9 lacking neutralizing activity, did not show reactivity.

Figure 7:
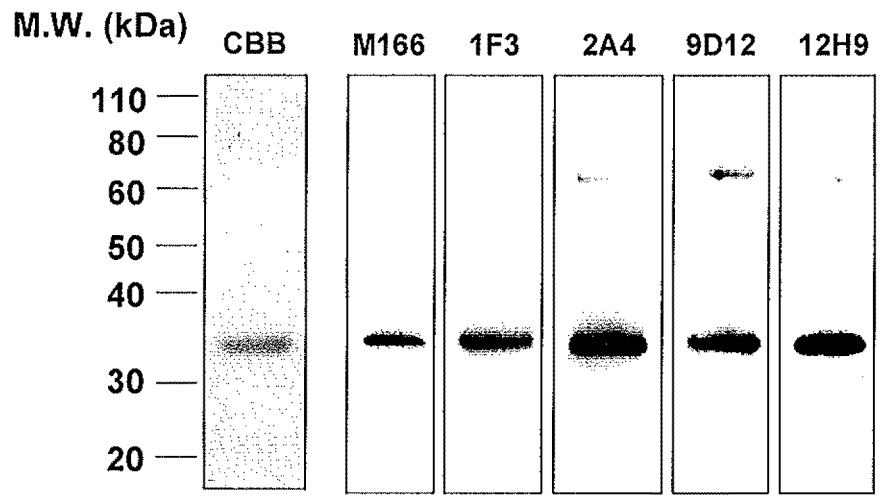
FIG. 7 shows reactivity with full-length PcrV and truncated PcrV in PcrV antibodies (1F3, 2A4, 9D12, 12H9 and Mab166) in Western blotting.
Figure 7:
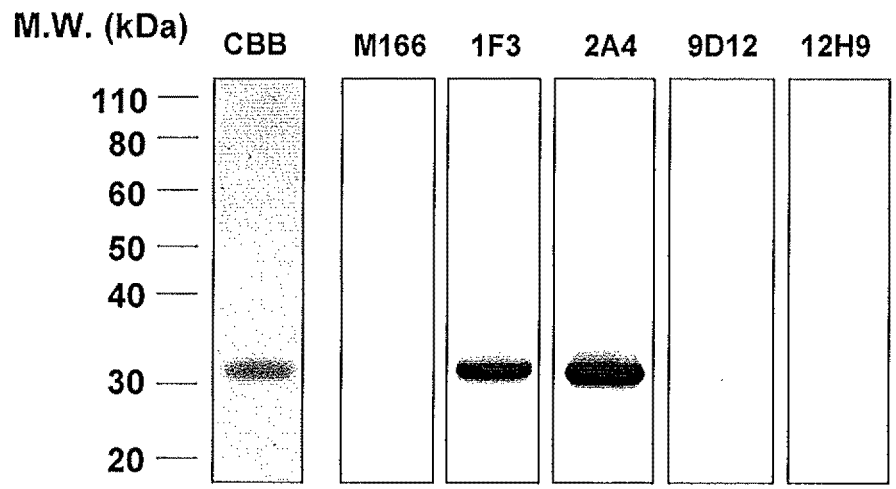

Binding analysis by Western blotting was also conducted. Purified recombinant PcrV protein was applied to SDS-PAGE, and then transferred to PVDF membrane. The transferred membrane was blocked with PBS containing 2% Block Ace (available from Dainippon Sumitomo Pharma Co., Ltd.) at room temperature for 2 hours under shaking. PcrV antibody solution diluted into 1 µg/mL was added to the membrane, allowed to react overnight at 4° C., and then washed with washing buffer B (10 mM phosphate buffer (pH 7.4), 0.05% Tween 20). As secondary antibody, HRP labeled anti-mouse IgG antibody (available from GE Healthcare) solution was added to the membrane, and allowed to react for 2 hours at room temperature. Thereafter, the membrane was washed with washing buffer B, and the signal was detected by ECL Plus Western Blot Detection System (available from GE Healthcare) (FIG. 7). While PcrV neutralization antibodies 1F3 and 2A4 reacted with both of full-length PcrV and truncated PcrV (136-233), Mab166 as well as 9D12 and 12H9 reacted only with full-length PcrV, and did not react with truncated PcrV (136-233).

This demonstrated that epitope region of PcrV neutralization antibodies 1F3 and 2A4 was a region corresponding to amino acid residues 136-233, and Mab166, 9D12 and 12H9 did not exclusively have an epitope region corresponding to amino acid residues 136-233.

Example 6

Correlation Between Specific Region of PcrV Protein and Strength of Cytotoxicity Using full-length PcrV protein (SEQ ID NO: 1) and truncated PcrV protein (having amino acid sequence corresponding to positions 136 to 233 in SEQ ID NO:1), suppression test of cytotoxicity inhibiting activity in 1F3, 2A4 and Mab166 were conducted in the following manner.

First, 1F3, 2A4 and Mab166 were adjusted to 1.56-6.25 nM, 6.25-25 nM and 50-200 nM, respectively, and 10 μL of these antibodies were added to the 96-well plate. For each test concentration range, each 10 μL of full-length PcrV protein or truncated PcrV protein in molar ratios of 30, 10, 3, 1 and 0.3 folds was added to 96-well plate, and kept still for 30 minutes at room temperature. Next, myeloma cell P3U1 was prepared into $5 \times 10^6$ cells/mL in cell culture medium (RPMI1640 containing sodium hydrogen carbonate, and not containing L glutamine and phenol red (available from Sigma)), and each 70 μL was added to the 96-well microplate. Further, a bacterial liquid of Pseudomonas aeruginosa strain SR24 cultured overnight in Mueller Hinton Broth (Difco) adjusted to be $1 \times 10^8$ cfu/mL was added in an amount of 10 μL/well, and cultured for 3 hours at 37° C. in the presence of 5% $CO_2$. After lapse of 3 hours, each 10 μL of WST-8 (available from Kishida Chemical Co., Ltd.) was added, and cultured at 37° C. in the presence of 5% $CO_2$ for 3 hours. After completion of culture, absorbance was measured at a wavelength of 450 nm.

Figure 8A:
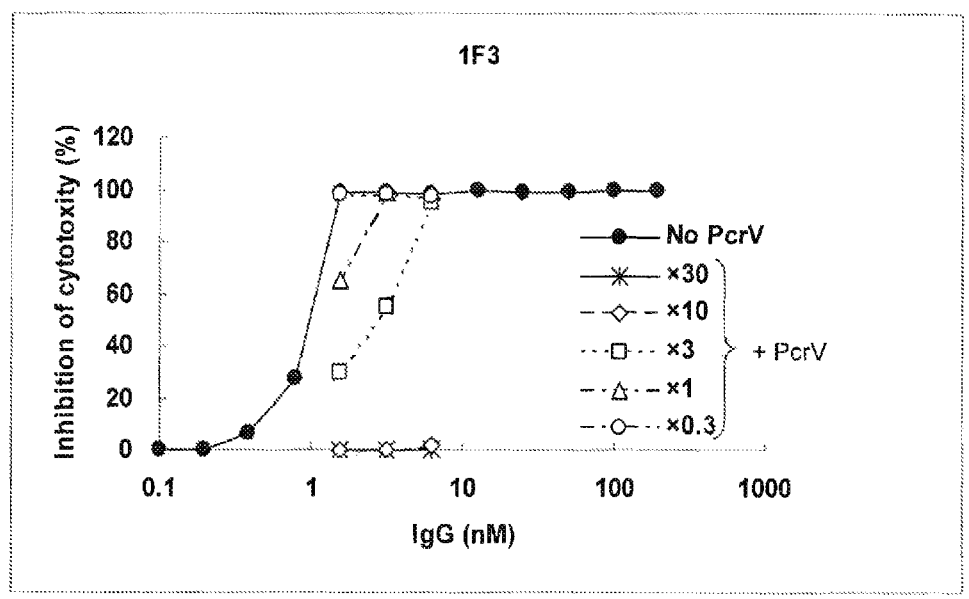
FIGS. 8A through 8C show correlation between antibody and full-length PcrV by suppression of cytotoxicity inhibiting activity.
Figure 8B:
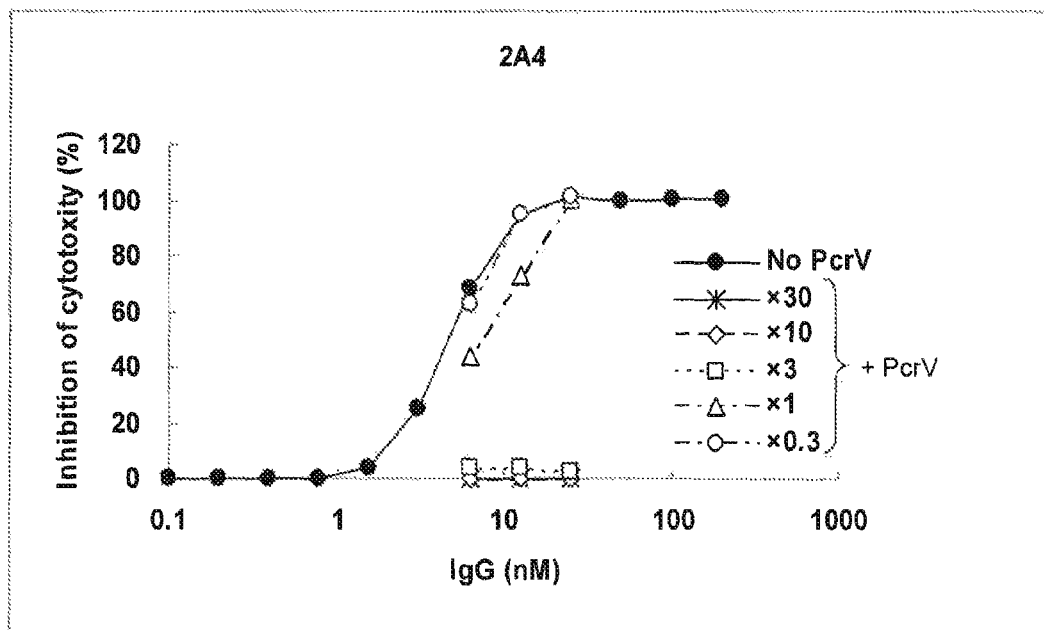
Figure 8C:
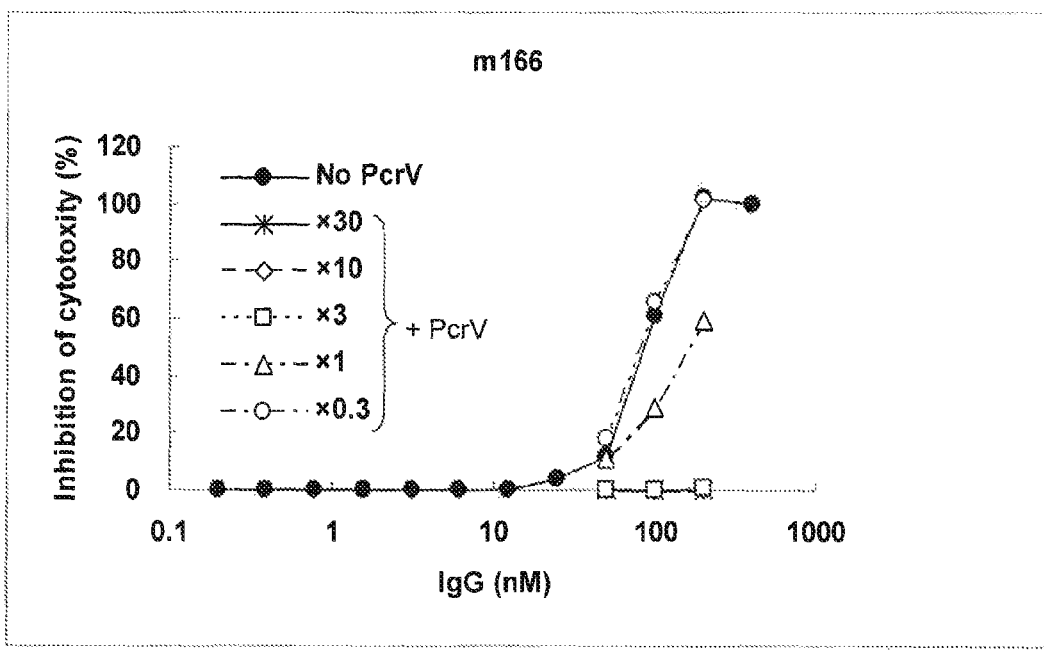
Figure 9A:
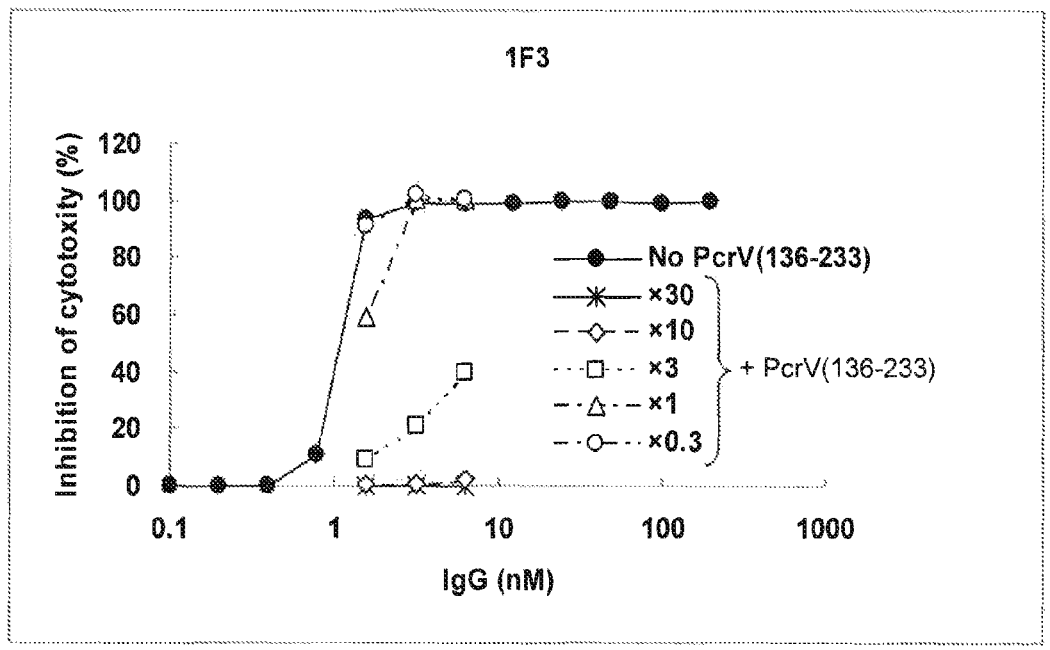
FIGS. 9A through 9C show correlation between antibody and truncated PcrV by suppression of cytotoxicity inhibiting activity.
Figure 9B:
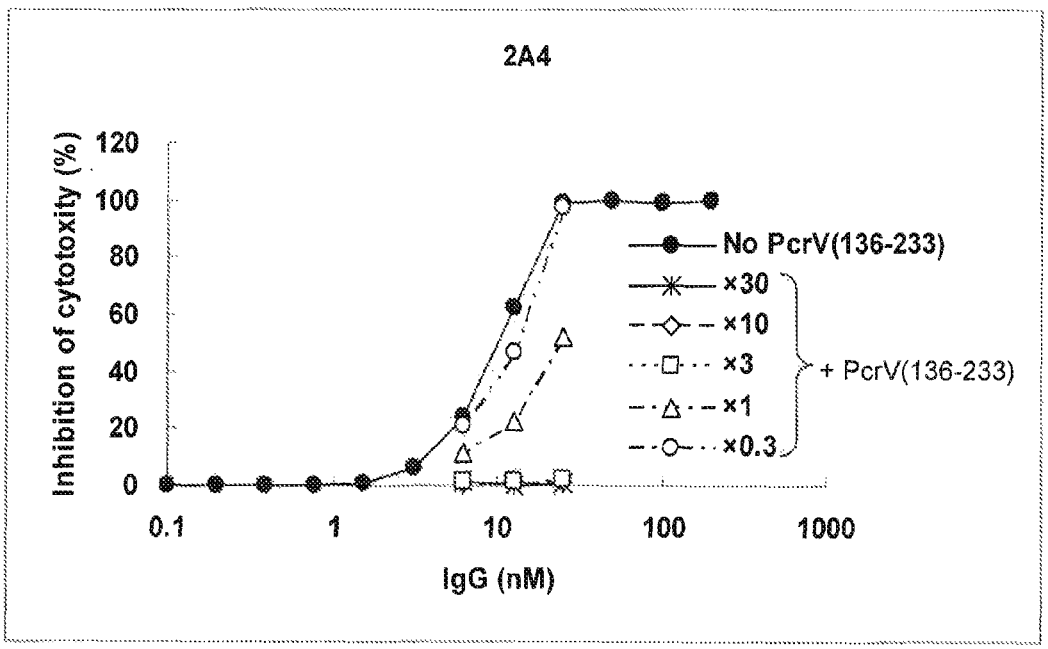
Figure 9C:
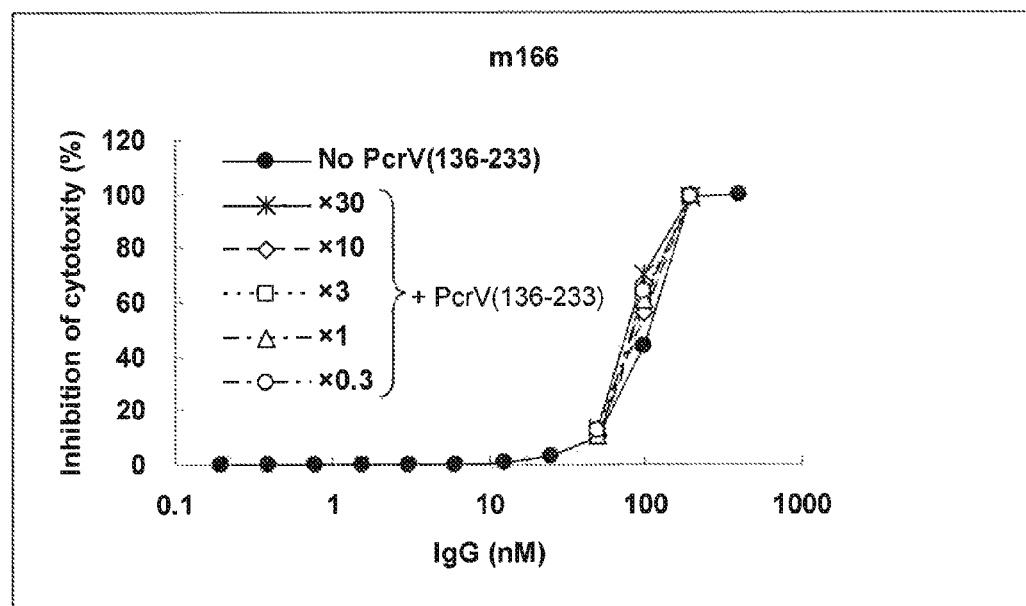

As a result, 1F3 and 2A4 exhibited higher cytotoxicity inhibition activity than Mab166. When full-length PcrV protein was added, the inhibition effects of anti-PcrV antibodies were suppressed in a PcrV dose-dependent manner (FIGS. 8A through 8C). When truncated PcrV (136-233) protein was added, the inhibition activities of 1F3 and 2A4 were also suppressed in a dose-dependent manner. On the other hand, the inhibition activity of Mab166 did not change by addition of truncated PcrV (136-233) (FIGS. 9A through 9C).

From these results, it can be considered that antibodies recognizing an epitope in amino acid residues 136-233 (1F3 and 2A4) have higher cytotoxicity inhibition activity than antibodies recognizing the different epitopes (e.g Mab166). In other words, it can be concluded that cytotoxicity inhibiting activity depends on the epitope region recognized by PcrV antibody, and the antibody reacts with 136-233 region of PcrV protein has a strong neutralizing ancitivity.

Example 7

Analysis of Amino Acid Sequence of PcrV Antibody (1F3 and 2A4)

From the established hybridoma cells, RNA was extracted using RNeasy Mini Kit (available from QIAGEN). From 1 μg of extracted RNA, DNA fragment was amplified using 5'RACE System for Rapid Amplification of cDNA Ends, Version 2.0 (available from Invitrogen). At this time, primers used for synthesis of cDNA were TAGAGTCACCGAG-GAGCCAGTTGT (SEQ ID NO: 7) for 1F3, and TCCA-GAGTTCCAAGTCACAGTCAC (SEQ ID NO: 8) for 2A4. Primers used in 5'RACE method were AGGGGCCAGTG-GATAGACCGATGGGGCTGT (SEQ ID NO: 9) for 1F3, and AGGGGCCAGTGGATAGACTGATGGGGGTGT (SEQ ID NO: 10) for 2A4. The amplified fragments were cloned by TOPO TA Cloning Kit (available from Invitrogen), and sequenced by Applied Biosystems 3130 Genetic Analyzer (available from Applied Biosystems). Analytical result is shown in FIG. 10 for IF3 and in FIG. 11 for 2A4.

Industrial Applicability

The monoclonal antibody of the present invention or a part thereof not only had high affinity with PcrV, but also exhibited strong inhibiting activity on cytotoxicity to eukaryotic cell of *Pseudomonas aeruginosa*. Therefore, the pharmaceutical composition containing the monoclonal antibody or a part thereof is useful as a therapeutic drug for *Pseudomonas aeruginosa*-related infection which is currently considered as being difficult to be treated in medical field.

---

The invention claimed is:

1. A monoclonal antibody or an antibody fragment thereof, having its recognition epitope at positions of 136 to 233 in amino acid sequence of SEQ ID NO: 1.

2. A monoclonal antibody or antibody fragment thereof according to claim 1, comprising the amino acid sequences of the complementarity determining regions of the monoclonal antibody produced by the hybridoma deposited as accession number FERM BP-11085 or the hybridoma deposited as accession number FERM BP-11086.

3. A monoclonal antibody according to claim 1, which is produced by the hybridoma deposited as accession number of FERM BP-11085 or the hybridoma deposited as accession number of FERM BP-11086.

4. A monoclonal antibody or antibody fragment thereof according to claim 1, having
   1) in the heavy chain variable region, complementarity determining regions including the amino acid sequences SFTSYWMH (SEQ ID NO: 15), INPSNGRTNYNEKFNT (SEQ ID NO: 16) and YGNYVVYYTMDY (SEQ ID NO: 17); and
   2) in the light chain variable region, complementarity determining regions including the amino acid sequences SASTSVSYME (SEQ ID NO: 18), TTSKLAS (SEQ ID NO: 19) and HQWRNYPFT (SEQ ID NO: 20).

5. A monoclonal antibody or antibody fragment thereof according to claim 1, having
   1) in the heavy chain variable region, complementarity determining regions including the amino acid sequences SITSDYAWN (SEQ ID NO: 21), YITYNGDTSYNPSLKS (SEQ ID NO: 22) and SRNYYGAWFAY (SEQ ID NO: 23); and
   2) in the light chain variable region, complementarity determining regions including the amino acid sequences KASQYVGTTVA (SEQ ID NO: 24), RASTRHT (SEQ ID NO: 25) and QQYCSSPLT (SEQ ID NO: 26).

6. A monoclonal antibody or antibody fragment thereof according to claim 1, having 1) a heavy chain variable region having the amino acid sequence of SEQ ID NO: 11, and
2) a light chain variable region having the amino acid sequence of SEQ ID NO: 12.

7. A monoclonal antibody or antibody fragment thereof according to claim 1, having
1) a heavy chain variable region having the amino acid sequence of SEQ ID NO: 13, and
2) a light chain variable region having the amino acid sequence of SEQ ID NO: 14.

8. A pharmaceutical composition comprising the antibody or antibody fragment thereof according to any one of claims 1 and 2-7 as an active ingredient and a pharmaceutically acceptable carrier.

9. The antibody fragment according to claim 1 that is a Fab, F(ab')$_2$ or scFV fragment.

10. The antibody fragment according to claim 4 that is a Fab, F(ab')$_2$ or scFV fragment.

11. The antibody fragment according to claim 5 that is a Fab, F(ab')$_2$ or scFV fragment.

12. The antibody fragment according to claim 6 that is a Fab, F(ab')$_2$ or scFV fragment.

13. The antibody fragment according to claim 7 that is a Fab, F(ab')$_2$ or scFV fragment.

* * * * *

UNITED STATES PATENT AND TRADEMARK OFFICE
CERTIFICATE OF CORRECTION

| | | |
|---|---|---|
| PATENT NO. | : 8,501,179 B2 | Page 1 of 1 |
| APPLICATION NO. | : 12/863983 | |
| DATED | : August 6, 2013 | |
| INVENTOR(S) | : Numata et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 259 days.

Signed and Sealed this
Eighteenth Day of August, 2015

Michelle K. Lee
*Director of the United States Patent and Trademark Office*

SEQUENCE LISTING

```
<160> NUMBER OF SEQ ID NOS: 26

<210> SEQ ID NO 1
<211> LENGTH: 294
<212> TYPE: PRT
<213> ORGANISM: Pseudomonas aeruginosa

<400> SEQUENCE: 1

Met Glu Val Arg Asn Leu Asn Ala Ala Arg Glu Leu Phe Leu Asp Glu
1               5                   10                  15

Leu Leu Ala Ala Ser Ala Ala Pro Ala Ser Ala Glu Gln Glu Glu Leu
            20                  25                  30

Leu Ala Leu Leu Arg Ser Glu Arg Ile Val Leu Ala His Ala Gly Gln
        35                  40                  45

Pro Leu Ser Glu Ala Gln Val Leu Lys Ala Leu Ala Trp Leu Leu Ala
    50                  55                  60

Ala Asn Pro Ser Ala Pro Pro Gly Gln Gly Leu Glu Val Leu Arg Glu
65                  70                  75                  80

Val Leu Gln Ala Arg Arg Gln Pro Gly Ala Gln Trp Asp Leu Arg Glu
                85                  90                  95

Phe Leu Val Ser Ala Tyr Phe Ser Leu His Gly Arg Leu Asp Glu Asp
            100                 105                 110

Val Ile Gly Val Tyr Lys Asp Val Leu Gln Thr Gln Asp Gly Lys Arg
        115                 120                 125
```

-continued

```
Lys Ala Leu Leu Asp Glu Leu Lys Ala Leu Thr Ala Glu Leu Lys Val
            130                 135                 140

Tyr Ser Val Ile Gln Ser Gln Ile Asn Ala Ala Leu Ser Ala Lys Gln
145                 150                 155                 160

Gly Ile Arg Ile Asp Ala Gly Gly Ile Asp Leu Val Asp Pro Thr Leu
                165                 170                 175

Tyr Gly Tyr Ala Val Gly Asp Pro Arg Trp Lys Asp Ser Pro Glu Tyr
            180                 185                 190

Ala Leu Leu Ser Asn Leu Asp Thr Phe Ser Gly Lys Leu Ser Ile Lys
            195                 200                 205

Asp Phe Leu Ser Gly Ser Pro Lys Gln Ser Gly Glu Leu Lys Gly Leu
210                 215                 220

Ser Asp Glu Tyr Pro Phe Glu Lys Asp Asn Asn Pro Val Gly Asn Phe
225                 230                 235                 240

Ala Thr Thr Val Ser Asp Arg Ser Arg Pro Leu Asn Asp Lys Val Asn
                245                 250                 255

Glu Lys Thr Thr Leu Leu Asn Asp Thr Ser Ser Arg Tyr Asn Ser Ala
            260                 265                 270

Val Glu Ala Leu Asn Arg Phe Ile Gln Lys Tyr Asp Ser Val Leu Arg
            275                 280                 285

Asp Ile Leu Ser Ala Ile
    290
```

<210> SEQ ID NO 2
<211> LENGTH: 885
<212> TYPE: DNA
<213> ORGANISM: Pseudomonas aeruginosa

<400> SEQUENCE: 2

```
atggaagtca gaaaccttaa tgccgctcgc gagctgttcc tggacgagct cctggccgcg    60
tcggcggcgc ctgccagtgc cgagcaggag gaactgctgg ccctgttgcg cagcgagcgg   120
atcgtgctgg cccacgccgg ccagccgctg agcgaggcgc aagtgctcaa ggcgctcgcc   180
tggttgctcg cggccaatcc gtccgcgcct ccggggcagg cctcgaggt actccgcgaa    240
gtcctgcagg cacgtcggca gcccggtgcg cagtgggatc tgcgcgagtt cctggtgtcg   300
gcctatttca gcctgcacgg gcgtctcgac gaggatgtca tcggtgtcta caaggatgtc   360
ctgcagaccc aggacggcaa gcgcaaggcg ctgctcgacg agctcaaggc gctgaccgcg   420
gagttgaagg tctacagcgt gatccagtcg cagatcaacg ccgcgctgtc ggccaagcag   480
ggcatcagga tcgacgctgg cggtatcgat ctggtcgacc ccacgctata tggctatgcc   540
gtcggcgatc ccaggtggaa ggacagcccc gagtatgcgc tgctgagcaa tctggatacc   600
ttcagcggca agctgtcgat caaggatttt ctcagcggct cgccgaagca gagcggggag   660
ctcaagggcc tcagcgatga gtaccccttc gagaaggaca caaacccggt cggcaatttc   720
gccaccacgg tgagcgaccg ctcgcgtccg ctgaacgaca aggtcaacga agagaccacc   780
ctgctcaacg acaccagctc ccgctacaac tcggcggtcg aggcgctcaa ccgcttcatc   840
cagaaatacg acagcgtcct gcgcgacatt ctcagcgcga tctag              885
```

<210> SEQ ID NO 3
<211> LENGTH: 33
<212> TYPE: DNA
<213> ORGANISM: artificial
<220> FEATURE:
<223> OTHER INFORMATION: primer for amplifying PcrV coding sequence

<400> SEQUENCE: 3

-continued

```
attgcatgca tggaagtcag aaaccttaat gcc                                33

<210> SEQ ID NO 4
<211> LENGTH: 33
<212> TYPE: DNA
<213> ORGANISM: Artificial
<220> FEATURE:
<223> OTHER INFORMATION: primer for amplifying PcrV coding sequence

<400> SEQUENCE: 4
tatttcgaag atctagcgcg actcttacag cgc                                33

<210> SEQ ID NO 5
<211> LENGTH: 27
<212> TYPE: DNA
<213> ORGANISM: Artificial
<220> FEATURE:
<223> OTHER INFORMATION: primer for amplifying truncated PcrV coding
      sequence

<400> SEQUENCE: 5
gctcgaggat cccaaggcgc tgaccgc                                       27

<210> SEQ ID NO 6
<211> LENGTH: 23
<212> TYPE: DNA
<213> ORGANISM: Artificial
<220> FEATURE:
<223> OTHER INFORMATION: primer for amplifying truncated PcrV coding
      sequence

<400> SEQUENCE: 6
gttaagcttc tcgaagggta ctc                                           23

<210> SEQ ID NO 7
<211> LENGTH: 24
<212> TYPE: DNA
<213> ORGANISM: Artificial
<220> FEATURE:
<223> OTHER INFORMATION: primer for synthesis of cDNA of 1F3

<400> SEQUENCE: 7
tagagtcacc gaggagccag ttgt                                          24

<210> SEQ ID NO 8
<211> LENGTH: 24
<212> TYPE: DNA
<213> ORGANISM: Artificial
<220> FEATURE:
<223> OTHER INFORMATION: primer for synthesis of cDNA of 2A4

<400> SEQUENCE: 8
tccagagttc caagtcacag tcac                                          24

<210> SEQ ID NO 9
<211> LENGTH: 30
<212> TYPE: DNA
<213> ORGANISM: Artificial
<220> FEATURE:
<223> OTHER INFORMATION: primer for 5'RACE of 1F3

<400> SEQUENCE: 9
aggggccagt ggatagaccg atggggctgt                                    30

<210> SEQ ID NO 10
<211> LENGTH: 30
```

```
<212> TYPE: DNA
<213> ORGANISM: Artificial
<220> FEATURE:
<223> OTHER INFORMATION: primer for 5'RACE of 2A4

<400> SEQUENCE: 10
aggggccagt ggatagactg atgggggtgt                                          30

<210> SEQ ID NO 11
<211> LENGTH: 121
<212> TYPE: PRT
<213> ORGANISM: Artificial
<220> FEATURE:
<223> OTHER INFORMATION: VH of Antibody 1F3

<400> SEQUENCE: 11

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Ser Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Asn Thr Lys Ala Thr Leu Thr Val Asp Thr Ser Ser Thr Ala Tyr
65                  70                  75                  80

Met Gln Leu Ser Ser Leu Thr Ser Glu Asp Ser Ala Val Tyr Tyr Cys
                85                  90                  95

Val Leu Tyr Gly Asn Tyr Val Val Tyr Tyr Thr Met Asp Tyr Trp Gly
            100                 105                 110

Gln Gly Thr Ser Val Thr Val Ser Ser
        115                 120

<210> SEQ ID NO 12
<211> LENGTH: 109
<212> TYPE: PRT
<213> ORGANISM: Artificial
<220> FEATURE:
<223> OTHER INFORMATION: VL of Antibody 1F3

<400> SEQUENCE: 12

Gln Ile Val Leu Thr Gln Ser Pro Thr Ile Met Ser Ala Ser Leu Gly
1               5                   10                  15

Glu Glu Ile Thr Leu Thr Cys Ser Ala Ser Thr Ser Val Ser Tyr Met
            20                  25                  30

Glu Trp Tyr Gln Gln Lys Ser Gly Thr Ser Pro Lys Ile Leu Ile Tyr
        35                  40                  45

Thr Thr Ser Lys Leu Ala Ser Gly Val Pro Ser Arg Phe Ser Gly Ser
    50                  55                  60

Gly Ser Gly Thr Phe Tyr Ser Leu Thr Ile Ser Ser Val Glu Ala Glu
65                  70                  75                  80

Asp Ala Ala Asp Tyr Tyr Cys His Gln Trp Arg Asn Tyr Pro Phe Thr
                85                  90                  95

Phe Gly Ser Gly Thr Lys Leu Glu Ile Lys Arg Ala Asp
            100                 105

<210> SEQ ID NO 13
<211> LENGTH: 120
<212> TYPE: PRT
<213> ORGANISM: Artificial
<220> FEATURE:
```

<223> OTHER INFORMATION: VH of Antibody 2A4

<400> SEQUENCE: 13

Asp Val Gln Leu Gln Glu Ser Gly Pro Gly Leu Val Lys Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Asn Gly Asp Thr Ser Tyr Asn Pro Ser Leu
    50                  55                  60

Lys Ser Arg Ile Ser Ile Ala Arg Asp Thr Ser Lys Asn Gln Phe Phe
65                  70                  75                  80

Leu Gln Leu Asn Ser Val Thr Thr Glu Asp Thr Ala Thr Tyr Ser Cys
                85                  90                  95

Ala Gly Ser Arg Asn Tyr Tyr Gly Ala Trp Phe Ala Tyr Trp Gly Gln
            100                 105                 110

Gly Thr Leu Val Thr Val Ser Ala
        115                 120

<210> SEQ ID NO 14
<211> LENGTH: 110
<212> TYPE: PRT
<213> ORGANISM: Artificial
<220> FEATURE:
<223> OTHER INFORMATION: VL of Antibody 2A4

<400> SEQUENCE: 14

Asp Ile Val Met Thr Gln Ser His Lys Phe Met Ser Thr Ser Ile Gly
1               5                   10                  15

Asp Arg Val Ser Ile Asn Tyr Lys Ala Ser Gln Tyr Val Gly Thr Thr
            20                  25                  30

Val Ala Trp Tyr Gln Gln Lys Ser Gly His Ser Pro Lys Leu Leu Ile
        35                  40                  45

Tyr Arg Ala Ser Thr Arg His Thr Gly Val Pro Asp Arg Phe Thr Gly
    50                  55                  60

Ser Gly Ser Gly Thr Asp Phe Thr Leu Asn Ile Ser Asn Val Gln Ser
65                  70                  75                  80

Glu Asp Leu Ala Asp Tyr Phe Cys Gln Gln Tyr Cys Ser Ser Pro Leu
                85                  90                  95

Thr Phe Gly Ala Gly Thr Tyr Leu Glu Val Lys Arg Ala Asp
            100                 105                 110

<210> SEQ ID NO 15
<211> LENGTH: 8
<212> TYPE: PRT
<213> ORGANISM: Artificial
<220> FEATURE:
<223> OTHER INFORMATION: CDR1 of 1F3 heavy chain

<400> SEQUENCE: 15

Ser Phe Thr Ser Tyr Trp Met His
1               5

<210> SEQ ID NO 16
<211> LENGTH: 16
<212> TYPE: PRT
<213> ORGANISM: Artificial
<220> FEATURE:
<223> OTHER INFORMATION: CDR2 of 1F3 heavy chain

```
<400> SEQUENCE: 16

Ile Asn Pro Ser Asn Gly Arg Thr Asn Tyr Asn Glu Lys Phe Asn Thr
1               5                   10                  15

<210> SEQ ID NO 17
<211> LENGTH: 12
<212> TYPE: PRT
<213> ORGANISM: Artificial
<220> FEATURE:
<223> OTHER INFORMATION: CDR3 of 1F3 heavy chain

<400> SEQUENCE: 17

Tyr Gly Asn Tyr Val Val Tyr Tyr Thr Met Asp Tyr
1               5                   10

<210> SEQ ID NO 18
<211> LENGTH: 10
<212> TYPE: PRT
<213> ORGANISM: Artificial
<220> FEATURE:
<223> OTHER INFORMATION: CDR1 of 1F3 light chain

<400> SEQUENCE: 18

Ser Ala Ser Thr Ser Val Ser Tyr Met Glu
1               5                   10

<210> SEQ ID NO 19
<211> LENGTH: 7
<212> TYPE: PRT
<213> ORGANISM: Artificial
<220> FEATURE:
<223> OTHER INFORMATION: CDR2 of 1F3 light chain

<400> SEQUENCE: 19

Thr Thr Ser Lys Leu Ala Ser
1               5

<210> SEQ ID NO 20
<211> LENGTH: 9
<212> TYPE: PRT
<213> ORGANISM: Artificial
<220> FEATURE:
<223> OTHER INFORMATION: CDR3 of 1F3 light chain

<400> SEQUENCE: 20

His Gln Trp Arg Asn Tyr Pro Phe Thr
1               5

<210> SEQ ID NO 21
<211> LENGTH: 9
<212> TYPE: PRT
<213> ORGANISM: Artificial
<220> FEATURE:
<223> OTHER INFORMATION: CDR1 of 2A4 heavy chain

<400> SEQUENCE: 21

Ser Ile Thr Ser Asp Tyr Ala Trp Asn
1               5

<210> SEQ ID NO 22
<211> LENGTH: 16
<212> TYPE: PRT
<213> ORGANISM: Artificial
<220> FEATURE:
<223> OTHER INFORMATION: CDR2 of 2A4 heavy chain

<400> SEQUENCE: 22
```

```
Tyr Ile Thr Tyr Asn Gly Asp Thr Ser Tyr Asn Pro Ser Leu Lys Ser
1               5                   10                  15

<210> SEQ ID NO 23
<211> LENGTH: 11
<212> TYPE: PRT
<213> ORGANISM: Artificial
<220> FEATURE:
<223> OTHER INFORMATION: CDR3 of 2A4 heavy chain

<400> SEQUENCE: 23

Ser Arg Asn Tyr Tyr Gly Ala Trp Phe Ala Tyr
1               5                   10

<210> SEQ ID NO 24
<211> LENGTH: 11
<212> TYPE: PRT
<213> ORGANISM: Artificial
<220> FEATURE:
<223> OTHER INFORMATION: CDR1 of 2A4 light chain

<400> SEQUENCE: 24

Lys Ala Ser Gln Tyr Val Gly Thr Thr Val Ala
1               5                   10

<210> SEQ ID NO 25
<211> LENGTH: 7
<212> TYPE: PRT
<213> ORGANISM: Artificial
<220> FEATURE:
<223> OTHER INFORMATION: CDR2 of 2A4 light chain

<400> SEQUENCE: 25

Arg Ala Ser Thr Arg His Thr
1               5

<210> SEQ ID NO 26
<211> LENGTH: 9
<212> TYPE: PRT
<213> ORGANISM: Artificial
<220> FEATURE:
<223> OTHER INFORMATION: CDR3 of 2A4 light chain

<400> SEQUENCE: 26

Gln Gln Tyr Cys Ser Ser Pro Leu Thr
1               5
```